(12) United States Patent
Clark et al.

(10) Patent No.: US 7,009,840 B2
(45) Date of Patent: Mar. 7, 2006

(54) MOBILE CLINICAL WORKSTATION

(75) Inventors: Richard A. Clark, Atlanta, GA (US);
Michael R. Jacobs, Atlanta, GA (US);
Steven B. Flemig, Woodstock, GA (US)

(73) Assignee: LXE, Inc., Norcross, GA (US)

( * ) Notice: Subject to any disclaimer, the term of this patent is extended or adjusted under 35 U.S.C. 154(b) by 0 days.

(21) Appl. No.: 10/783,333

(22) Filed: Feb. 20, 2004

(65) Prior Publication Data

US 2004/0165348 A1    Aug. 26, 2004

Related U.S. Application Data

(63) Continuation of application No. 10/171,582, filed on Jun. 13, 2002, now Pat. No. 6,721,178, which is a continuation of application No. 09/397,817, filed on Sep. 17, 1999, now Pat. No. 6,493,220.

(60) Provisional application No. 60/100,976, filed on Sep. 18, 1998.

(51) Int. Cl.
*G06F 1/16* (2006.01)

(52) U.S. Cl. ..................... 361/686; 361/680; 361/681; 312/223.3; 248/918

(58) Field of Classification Search ........ 361/680–686; 248/161, 404, 676–678, 158, 370, 127, 129, 248/918–919; 312/223.1, 223.2, 223.3, 197, 312/239; 108/3, 25, 50.19, 147, 150, 50.11, 108/50.02; 606/32, 202
See application file for complete search history.

(56) References Cited

U.S. PATENT DOCUMENTS

D279,007 S    5/1985  Empson et al. ............ D14/113

(Continued)

FOREIGN PATENT DOCUMENTS

CH    688 607 A5    2/1995

(Continued)

OTHER PUBLICATIONS

Jaco, Inc. v. EMS Technologies, Inc., LXE, Inc. and FHS Acquisition, LLC; Civil Action No. 03-CV-11995 NG; "First Amended Complaint," filed Jan. 9, 2004.

(Continued)

*Primary Examiner*—Michael Datskovskiy
(74) *Attorney, Agent, or Firm*—Sutherland Asbill & Brennan, LLP

(57) ABSTRACT

A mobile workstation includes an adjustable-height horizontal tray and a pull-out keyboard tray mounted beneath the horizontal tray to support a keyboard. A device, such as computer terminal, mounts to the horizontal tray through installation into a vertically-mounted docking station mounted to the horizontal tray, or through a mounting bracket mounted adjacent to the horizontal tray. A tiltable bracket mounts the docking station to the horizontal tray, and a clutch assembly allows the angle of the bracket and the angle of the docking station and the computer terminal, to be adjusted to avoid glare on the terminal's display screen. With a mounting bracket, a tiltable bracket mounts a vertically-mounted display screen to the top of the horizontal tray. The mobile workstation also carries a power unit including an extended-life battery and a battery charger that connects to an AC power supply to charge the conventional battery pack connected to the computer terminal as well as the extended-life battery carried on the mobile workstation. When the computer terminal is stored in the mobile workstation, the wireless computer terminal can communicate through a radio transceiver in communication with a computer network, such a distributed patient-care computer network. Furthermore, a mobile workstation with a docking station includes a spring-mounted vertically-movable leveling tray that allows the computer terminal to be easily removed from the docking station using a push-down-and-tilt motion. An electronic and/or key lock selectively prevents vertical movement of the leveling tray to secure the computer terminal within the docking station.

8 Claims, 21 Drawing Sheets

U.S. PATENT DOCUMENTS

| | | | |
|---|---|---|---|
| 4,595,008 A | 6/1986 | Guibert | 128/399 |
| 4,640,199 A | 2/1987 | Zigman | 108/6 |
| D289,873 S | 5/1987 | Gemmell et al. | D14/113 |
| D295,415 S | 4/1988 | Thies et al. | D14/114 |
| 4,852,500 A | 8/1989 | Ryburg et al. | 108/105 |
| D310,358 S | 9/1990 | Nuttall et al. | D14/113 |
| D313,405 S | 1/1991 | Barry et al. | D14/113 |
| 4,989,291 A | 2/1991 | Parent | 15/315 |
| D317,912 S | 7/1991 | Takai | D14/113 |
| D319,435 S | 8/1991 | Brown | D14/113 |
| D326,847 S | 6/1992 | Savio | D14/113 |
| 5,174,223 A | 12/1992 | Nagy et al. | 108/50 |
| D337,104 S | 7/1993 | Orchard | D14/113 |
| D339,796 S | 9/1993 | Goodner et al. | D14/113 |
| 5,287,815 A | 2/1994 | Gross | 108/50 |
| D344,933 S | 3/1994 | Wiseman et al. | D14/113 |
| D349,489 S | 8/1994 | Wang | D14/113 |
| D354,052 S | 1/1995 | Imai | D14/113 |
| D354,952 S | 1/1995 | Rodd | D14/113 |
| D357,468 S | 4/1995 | Rodd | D14/113 |
| 5,436,792 A * | 7/1995 | Leman et al. | 361/686 |
| 5,473,997 A | 12/1995 | Solomon et al. | 108/93 |
| 5,536,084 A * | 7/1996 | Curtis et al. | 700/240 |
| 5,619,397 A * | 4/1997 | Honda et al. | 361/686 |
| 5,627,450 A * | 5/1997 | Ryan et al. | 361/686 |
| 5,630,566 A * | 5/1997 | Case | 248/122.1 |
| 5,633,782 A * | 5/1997 | Goodman et al. | 361/683 |
| 5,687,717 A | 11/1997 | Halpern et al. | 128/630 |
| 5,694,199 A | 12/1997 | Rodriguez | 351/223 |
| D393,382 S | 4/1998 | Rutter et al. | D6/474 |
| 5,751,548 A * | 5/1998 | Hall et al. | 361/686 |
| 5,772,637 A | 6/1998 | Heinzmann et al. | 604/248 |
| 5,806,943 A | 9/1998 | Dell et al. | 312/223.3 |
| 5,842,672 A | 12/1998 | Sweere et al. | 248/278.1 |
| 5,859,762 A * | 1/1999 | Clark et al. | 361/686 |
| 5,868,079 A | 2/1999 | Charoy | 108/7 |
| 5,899,421 A * | 5/1999 | Silverman | 248/175 |
| 5,918,841 A * | 7/1999 | Sweere et al. | 248/123.11 |
| 6,041,242 A * | 3/2000 | Coulthard | 455/575.1 |
| 6,061,104 A | 5/2000 | Vanicky et al. | 348/827 |
| 6,098,936 A | 8/2000 | Birrell | 248/122.1 |
| 6,102,284 A | 8/2000 | Myers et al. | 235/375 |
| 6,125,028 A * | 9/2000 | Matsumoto | 361/681 |
| 6,185,096 B1 * | 2/2001 | Helot et al. | 361/686 |
| 6,222,728 B1 * | 4/2001 | Jaggers et al. | 361/686 |
| 6,269,753 B1 | 8/2001 | Roddan | 108/50.01 |
| 6,298,794 B1 | 10/2001 | Brown et al. | 108/50.01 |
| 6,339,732 B1 * | 1/2002 | Phoon et al. | 700/237 |
| 6,394,402 B1 | 5/2002 | Coonan et al. | 248/123.11 |
| 6,447,451 B1 | 9/2002 | Wing et al. | 600/437 |
| 6,493,217 B1 | 12/2002 | Jenkins, Jr. | 361/683 |
| 6,654,378 B1 * | 11/2003 | Mahany et al. | 370/401 |
| 2002/0013640 A1 | 1/2002 | Phoon et al. | 700/237 |
| 2003/0019165 A1 | 1/2003 | Gallant et al. | 42/36.4 |
| 2003/0080655 A1 | 5/2003 | Goldberg | 312/290 |

FOREIGN PATENT DOCUMENTS

| | | |
|---|---|---|
| CH | 688607 | 12/1997 |
| DE | G 81 14 991.3 | 5/1981 |
| DE | 295 06 433 U1 | 4/1995 |
| DE | 195 36 664 | 4/1997 |
| DE | 19642425 A1 | 4/1998 |
| DE | 19650100 | 6/1998 |
| EP | 0 145 410 | 12/1983 |
| EP | 0 321 137 A2 | 12/1988 |
| EP | 0 145 410 A2 | 11/1996 |
| EP | 0796575 | 9/1997 |
| FI | 108774 B | 6/1999 |
| FI | 974408 | 6/1999 |
| JP | 05-161510 | 6/1993 |
| JP | 09-262137 | 10/1997 |
| JP | 10-11172 | 1/1998 |
| JP | 10-057157 | 3/1998 |
| JP | 10-146224 | 6/1998 |
| JP | 11-127976 | 5/1999 |
| WO | WO 97/46824 | 12/1997 |
| WO | WO 01/50914 A1 | 7/2001 |

OTHER PUBLICATIONS

Title: Medical Cart, Author: Mobile Computers & Mounts, Inc., 1 pg.
Title: Mobilize It, Author: MobilizeIt.com, 2 pgs.
Title: Computer Carts, Author Ergotron Inc., 2003 2 pgs.
Title: Wireless Mobile Retail Solutions, InfoLogix Mobile Computing Experts, 4 pgs.
Title: Leaders in Customer Care Professional Services, InfoLogix Mobile Computing Experts, 4 pgs.
Title: Wireless Healthcare solutions Focused on Patient Safety, InfoLogix Mobile Computing Experts, 4 pgs.
Title: Real-Time Technology Solutions, Designed to Provide the Highest level of Patient Care, InfoLogix Mobile Computing Experts, 5 pgs.
Title: Healthcare Informatics 2003 Resource Guide, InfoLogix, 3 pgs.
Title: Reconcile Gift Certificate Fraud, Integrated Solutions, Jun. 2003, 1 pg.

* cited by examiner

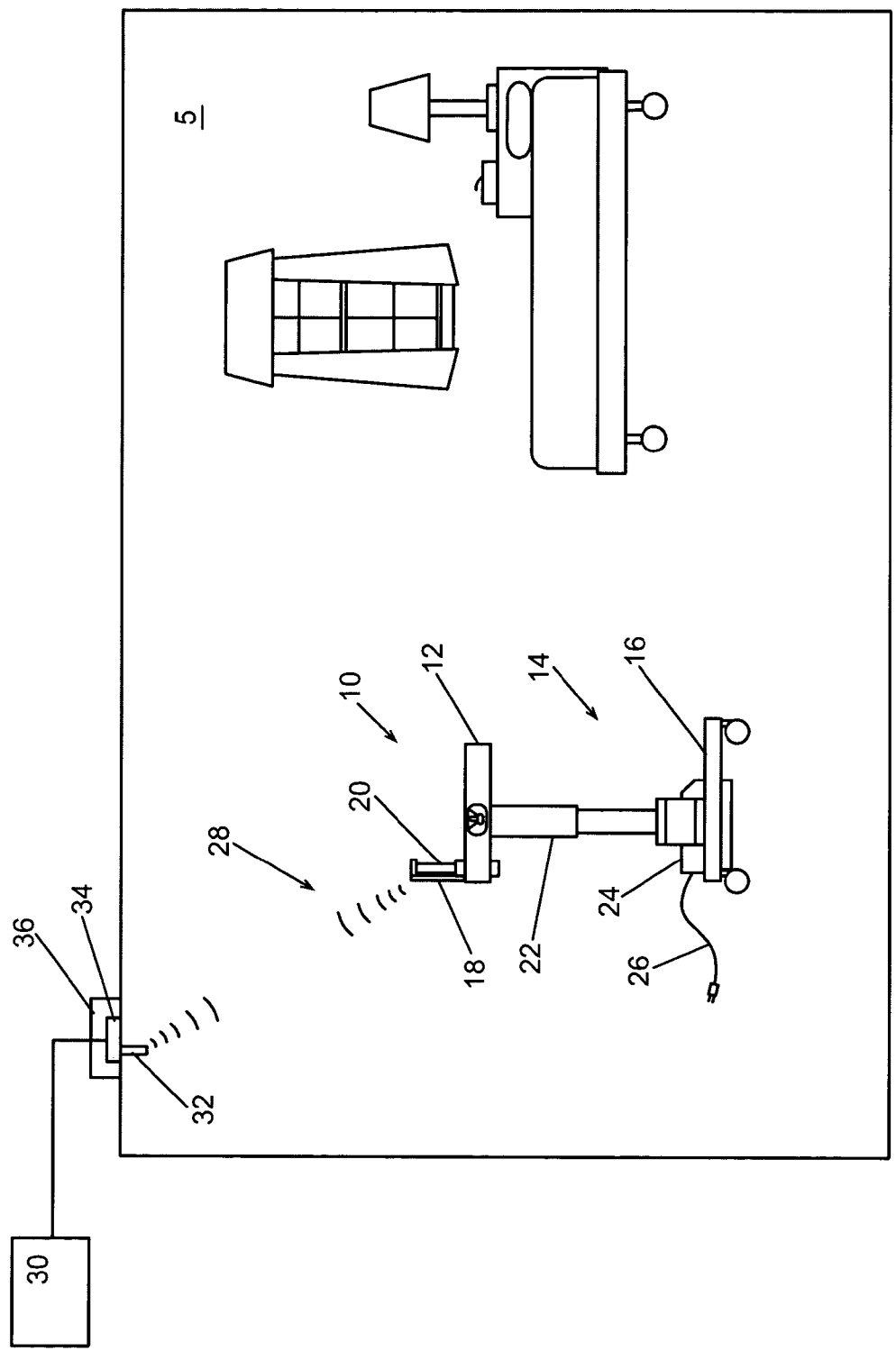

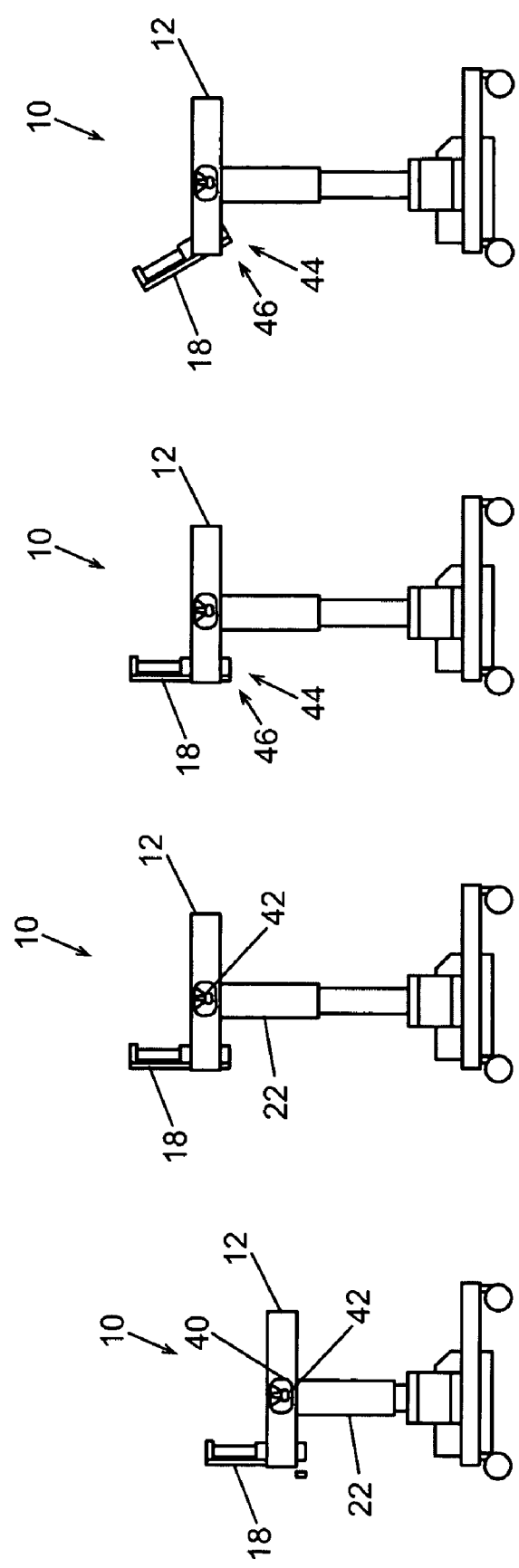

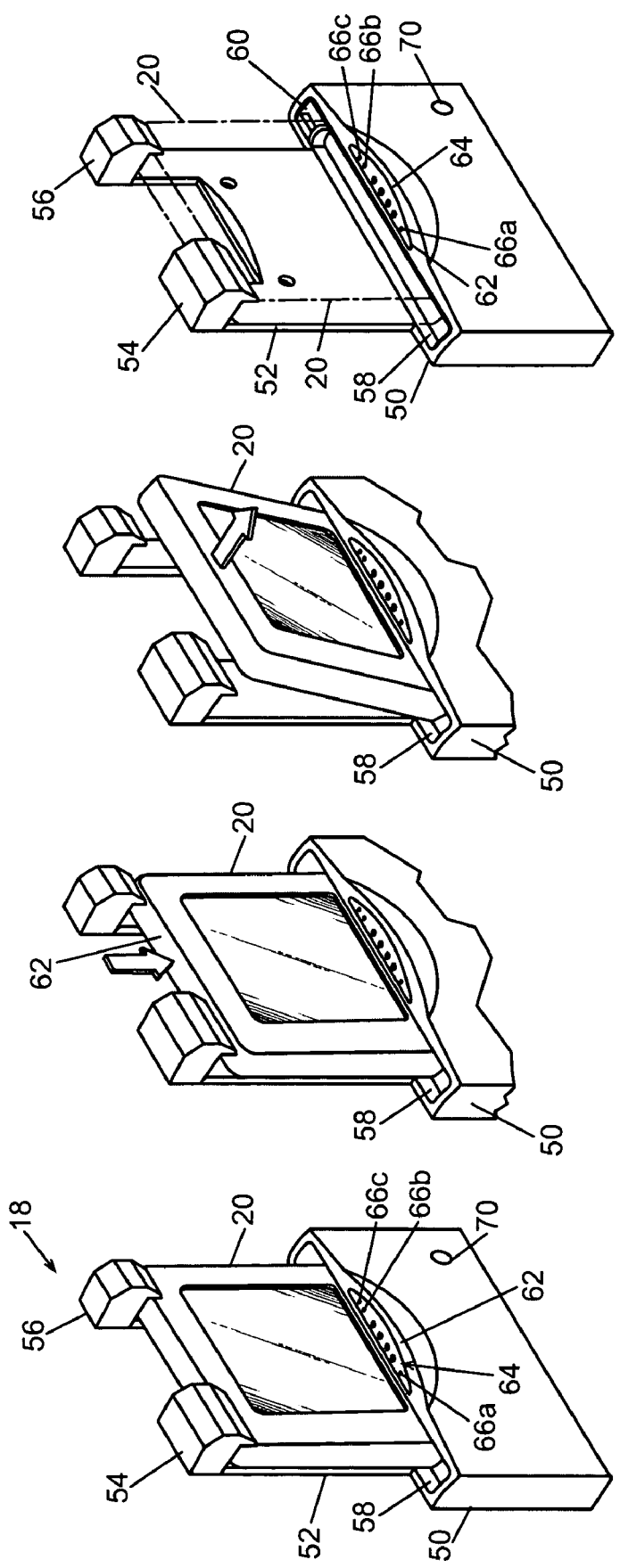

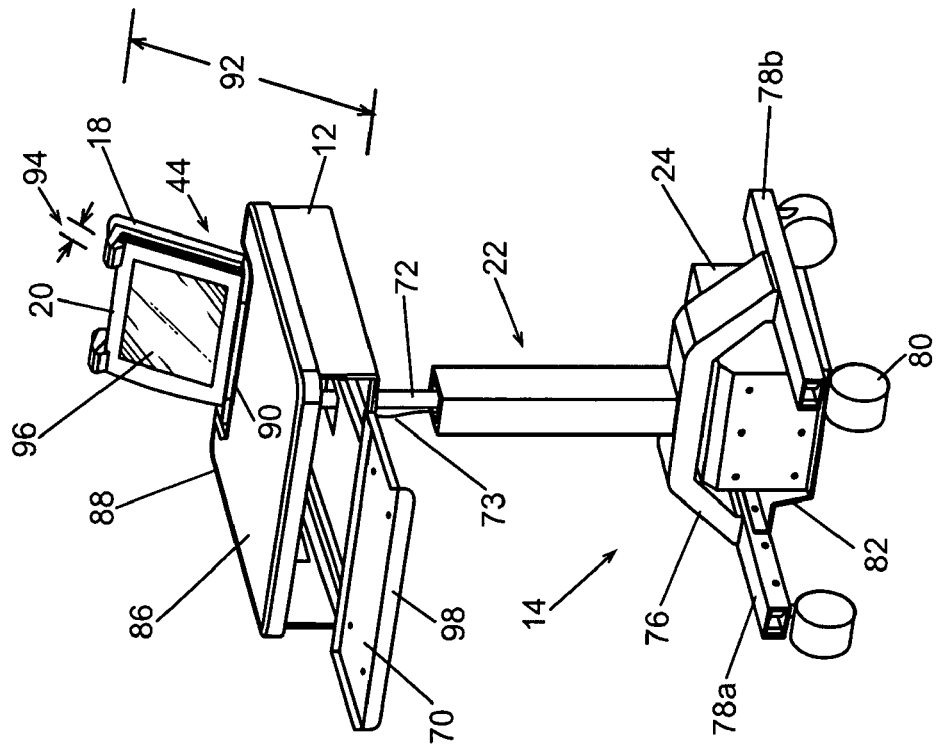
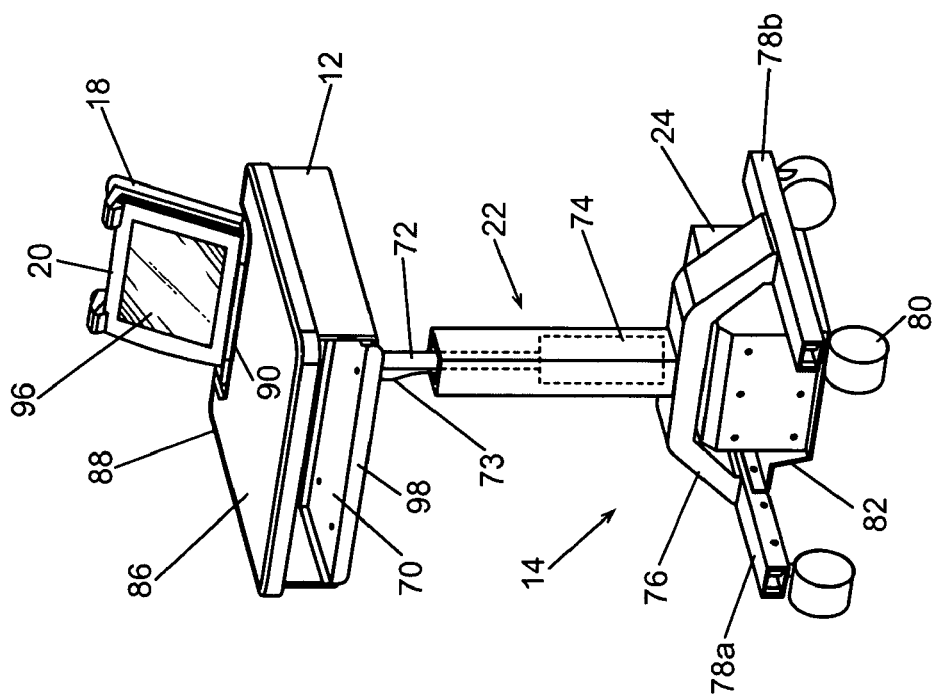

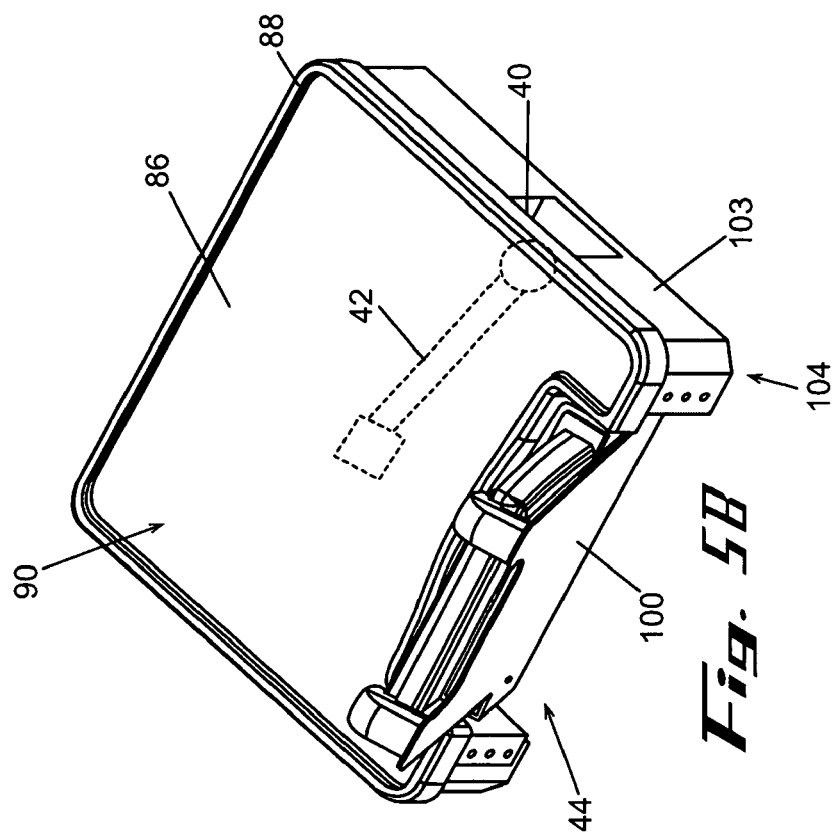
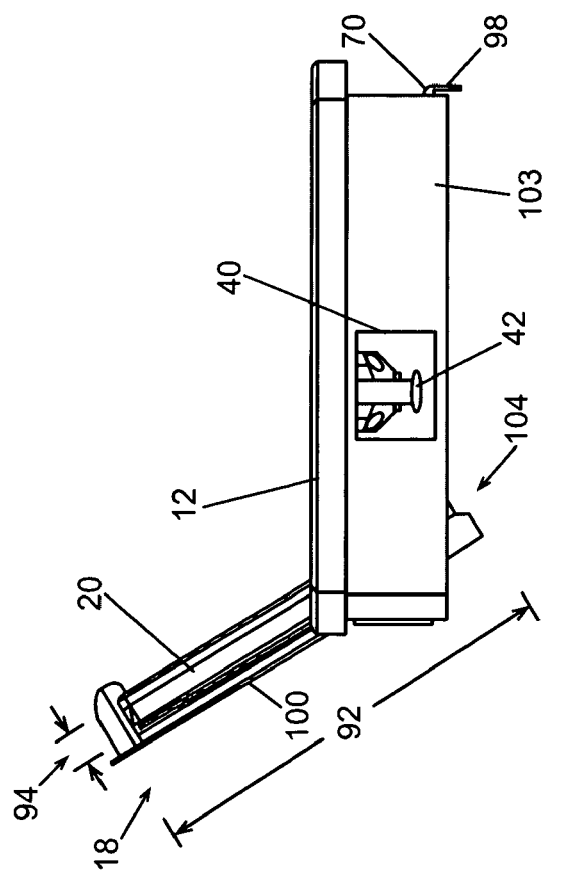

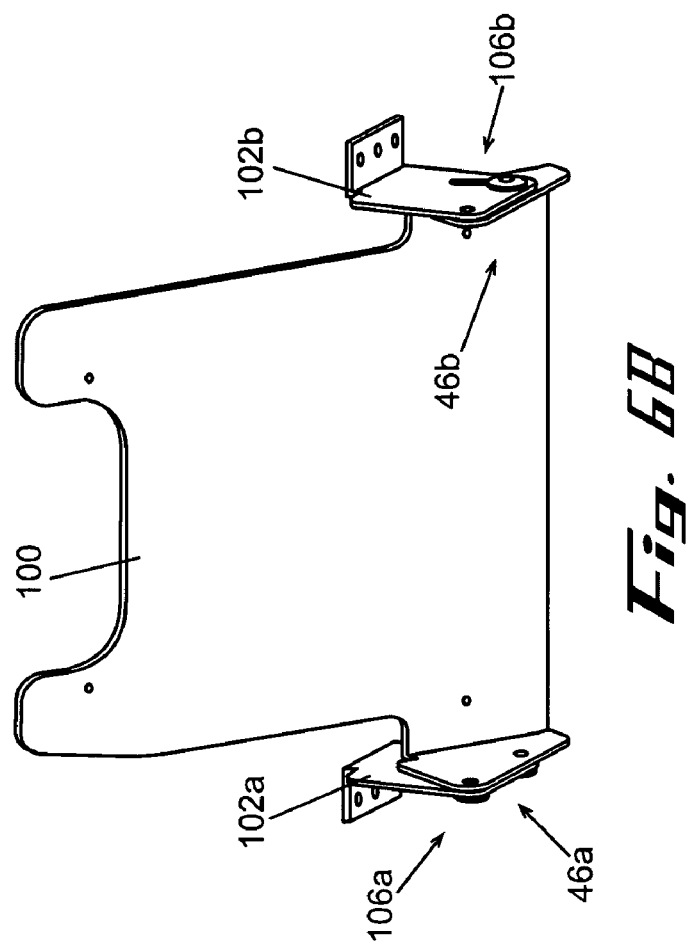
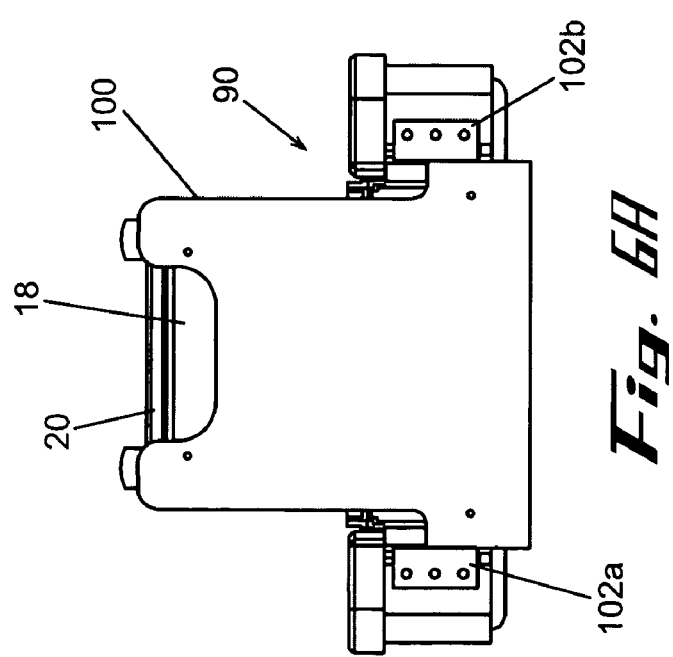

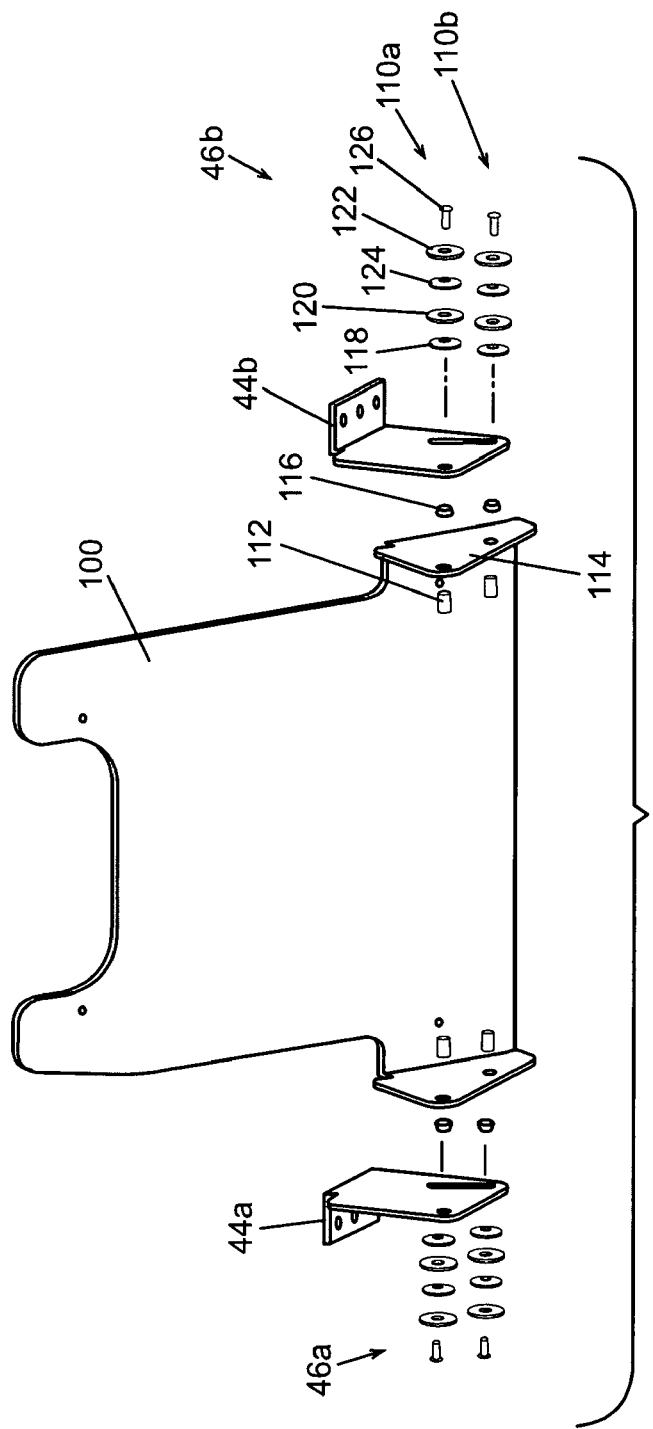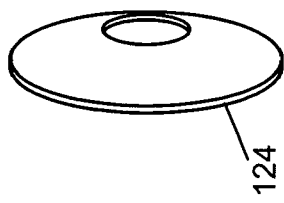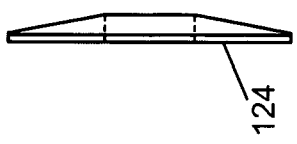

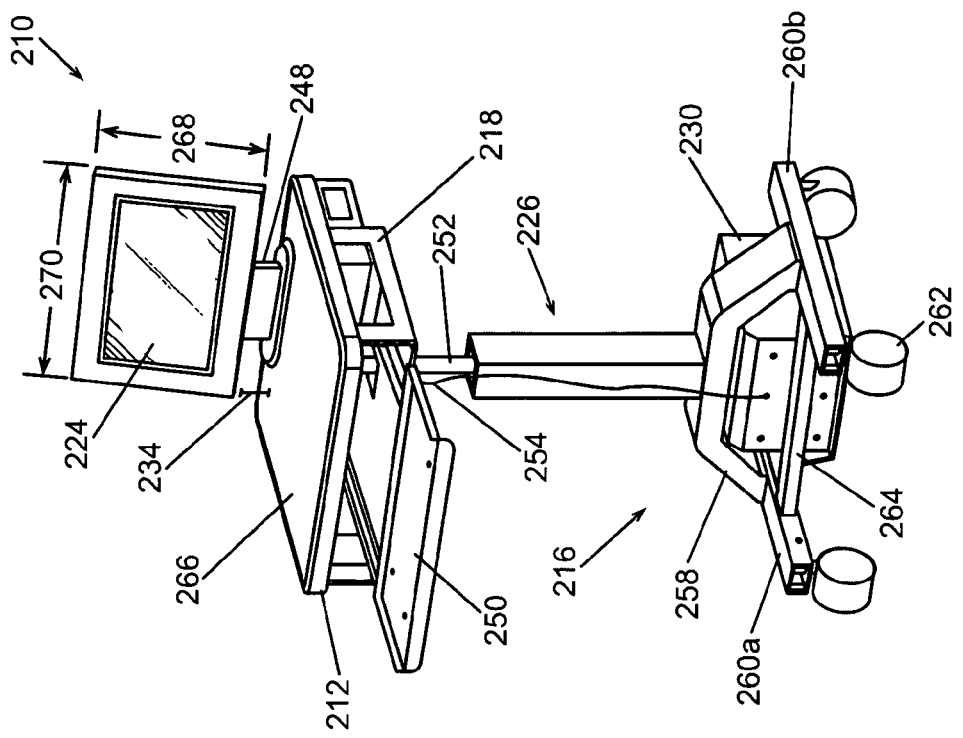
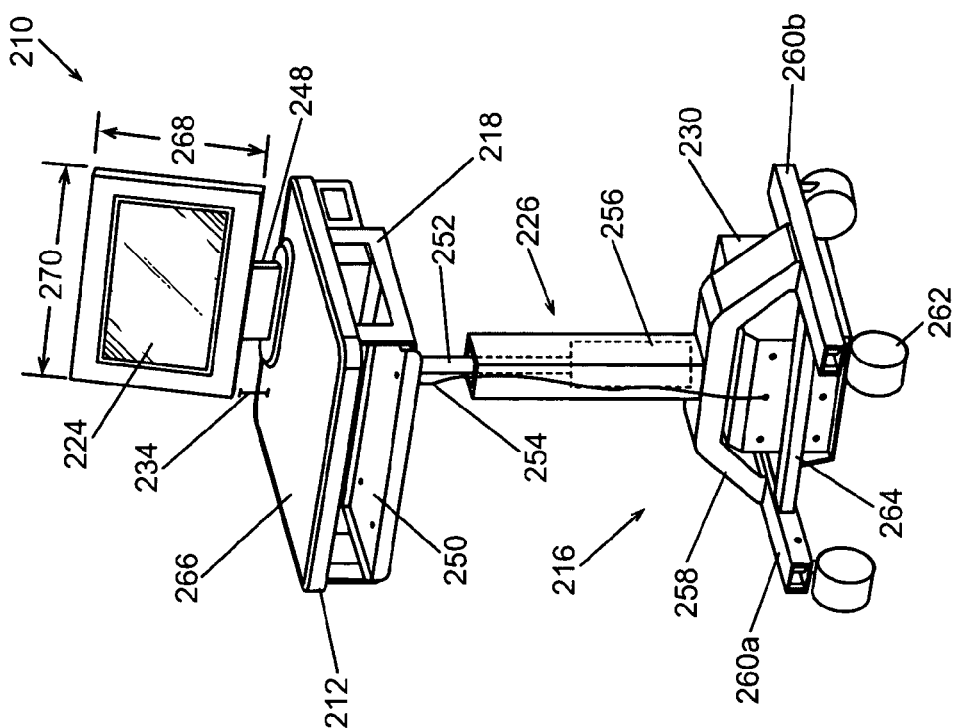

MOBILE CLINICAL WORKSTATION

The present application is a continuation of U.S. patent application Ser. No. 10/171,582, filed on Jun. 13, 2002 now U.S. Pat. No. 6,721,178, now allowed, which is a continuation of U.S. patent application Ser. No. 09/397,817, filed on Sep. 17, 1999, now U.S. Pat. No. 6,493,220. This application claims the benefit 60/100,976, filed Sep. 18, 1998.

TECHNICAL FIELD

This invention relates to mobile workstations and, more particularly, to a mobile workstation that can include an adjustable-height horizontal tray, a pull-out keyboard tray, a vertically-mounted docking station mounted to the tray, a computer terminal mounted beneath the tray, a display screen mounted to the horizontal tray, and a power unit.

BACKGROUND OF THE INVENTION

Wireless computer terminals are particularly well-suited to medical care environments, such as hospitals, doctors' offices, and nursing homes. Here, wireless computer terminals offer a great advantage by replacing the conventional clipboard hanging from a patient's bed frame or examination table with a wireless computer terminal that uses radio-frequency transmissions to communicate with a distributed computer network. These wireless computer terminals bring bedside medical care into the information age by computerizing medical charts.

A wireless computer terminal is typically used to post and retrieve the information that was traditionally posted on a bed-side clipboard, such as the patient's prescriptions, vital signs, receipt of medications, scheduled tests, etc. This and other information is now automatically communicated between the wireless computer terminal and a distributed patient-care computer network. A medical practitioner making the rounds, such as a doctor or nurse, usually picks up the wireless computer terminal from a fixed storage location before visiting the patient and takes the terminal into the patient's room. The practitioner then performs the indicated tasks and enters any relevant information into the wireless computer terminal, such as test results, vital signs, observations, and the like. When the visit with the patient is over, the practitioner usually returns the wireless computer terminal to its storage location.

Deploying a wireless computer terminal in this type of medical care environment presents several challenges. First, the wireless computer terminal should be stored near the patient's hospital or examination room for easy access by the medical practitioner. Second, the wireless computer terminal should be kept secure to prevent theft or tampering. Third, the wireless computer terminal should be easily accessible with one hand because a medical practitioner often has the other hand occupied, for example with a tray of medications, a medical instrument, or the like. Fourth, the battery inside a wireless terminal should be kept charged.

To address these needs, wireless computer terminals have been deployed in conjunction with wall-mounted cradles or docking stations located outside of patient hospital rooms. The wall-mounted cradle includes a key or electronic lock for selectively securing the computer terminal in the cradle. For example, the cradle may include a vertically movable leveling tray that allows the wireless terminal to be easily removed from, and replaced for storage within, the cradle with one hand using a push-down-and-tilt motion. A locking mechanism selectively prevents the leveling tray from moving vertically. A battery charger connected to an AC power supply charges the computer terminal's battery while the terminal is stored within the cradle.

These wall-mounted cradles work well but have a number of drawbacks. In particular, a separate wall-mounted cradle with an associated wireless computer terminal is typically located outside each hospital room. This results in a relatively large number of cradles and associated terminals, with each terminal sitting idle most of the day. Purchasing such a large number of cradles and associated terminals is expensive. In addition, once a practitioner removes the terminal from the cradle and takes it into the patient's hospital room, there may no place to conveniently store the terminal inside the hospital room. The practitioner may have to step back outside the patient's room to return the terminal to the cradle if both hands are needed for another activity during the visit, such as making the bed, assisting the patient to get out of bed, dressing a wound, or some other activity.

In another attempt to address some of the needs of medical practitioners, a mobile cart has been deployed in conjunction with a laptop computer. The mobile cart includes a horizontal tray with an upper surface on which the laptop computer resides. The laptop computer is typically secured on the mobile cart with a KENSINGTON lock (i.e., a cylinder-type key-operated mechanical lock). This mobile cart with an attached laptop computer has some advantages, but it also has a number of drawbacks. Physically walking back and forth from the patient's bedside to the mobile cart to enter patient information into the computer can be inconvenient. In many cases, a removable computer terminal that can be carried over to the patient's bedside would be more convenient. A removable computer terminal more closely resembles a conventional clipboard chart, which may be preferred by practitioners who have grown accustomed to clipboard charts.

In the previous mobile cart design, however, the practitioner must manually unlock the KENSINGTON lock to remove the laptop computer. This can be inconvenient, particularly when the medical practitioner is holding other items, such medical instruments. The KENSINGTON lock itself, which typically dangles from a cable connected to the computer, can be an annoyance. In addition, the location of the laptop computer on the surface of the cart occupies this space, which might be better used as a workspace for the practitioner to make notes, carry instruments, place medications, and so forth. The laptop computer also has a number of limitations. For example, the computer's battery life is typically about two to three hours, and recharging the battery typically requires plugging the laptop computer's power cord into an AC outlet for several hours. Plugging the laptop computer in for recharging typically idles the mobile cart for this period.

There is, therefore, a need for an improved docking station for a wireless computer terminal. Specifically, there is a need for a docking station that eliminates the need for a wall-mounted cradle and an associated wireless computer terminal located outside each patient hospital room. There is a further need for a mobile cart and associated computer terminal that is more convenient to use, has increased workspace, and has increased battery life.

SUMMARY OF THE INVENTION

The present invention meets the needs described above in a mobile workstation that includes a wheeled chassis, an adjustable-height horizontal tray, and a vertically-mounted docking station supported by the chassis or the horizontal tray. A medical practitioner making the rounds can push the mobile workstation from room to room and use the same computer terminal when attending each patient. An extended-life battery allows the mobile workstation to be used for an entire shift before recharging. The mobile workstation thus eliminates the need for locating a wall-mounted cradle and an associated wireless computer terminal outside each patient's room. Because the docking station is vertically mounted, the terminal does not occupy the top surface of the horizontal tray, which allows this area to be used as a work surface.

When a docking station is used, a vertically movable leveling tray allows the wireless terminal to be easily removed from, and replaced for storage within, the docking station with one hand. An electronic or key lock allows the docking station to be easily locked and unlocked with one hand. When a docking station is not used, the terminal may be mounted to the top or bottom side of the tray.

The docking station typically includes an elongate dimension and a relatively slender dimension, and the tray supports the docking station with the elongate dimension substantially vertical and the slender dimension substantially horizontal. The bracket may be tiltably connected to the tray for rotating the docking station relative to the tray. A clutch connecting the tiltable bracket to the tray maintains the docking station in a number of selectable rotational positions relative to the tray.

The docking station typically includes a retainer for holding the device in the docking station. The docking station also includes a restraining member movable from an open position to a closed position so that the device may be removed from the docking station when the restraining member is in the open position, and so that the device is resiliently restrained in the docking station when the restraining member is in the closed position. For example, the retainer may include two spaced-apart arms for receiving a first side of a computer terminal, and the restraining member may include a leveling tray for resiliently supporting a second side opposite the first side of the computer terminal. The docking station may also include a lock movable from a release position to an interference position to positively restrain the computer terminal in the docking station. In this case, the docking station also includes an unlocking device for selectively moving the lock from the interference position to the release position to allow the computer terminal to be removed from the docking station.

In an alternative embodiment, the mobile workstation includes a wheeled chassis and a tray supported by the chassis. The tray has an upper surface defining a substantially horizontal work surface. The mobile workstation also includes a bracket mounted adjacent to the work surface for supporting a docking station for holding a device, such as a computer terminal. The device typically includes a display screen, and the docking station supports the device with the display screen in a substantially vertical position above the work surface. The mobile workstation may also include a pull-out keyboard tray supported adjacent to a lower surface of the tray.

Another alternative configuration of a mobile workstation includes a wheeled chassis, an adjustable-height horizontal tray, a wireless computer terminal supported by the chassis or the horizontal tray, and a power unit supported on the chassis. The tray has an upper surface defining a substantially horizontal work surface. The mobile workstation also includes a front mounting bracket mounted beneath the work surface for supporting a device, such as a wireless computer terminal. The device typically includes or attaches to a display screen, with the display screen above and towards the rear of the work surface. The mobile workstation may also include a pull-out keyboard tray supported adjacent to a lower surface of the tray. The mobile workstation also includes a back mounting bracket mounted adjacent to and beneath the work surface for supporting a power converter. The power converter connects to a battery pack and provides power to the device and to the display screen.

For each alternative embodiment, the chassis of the mobile workstation includes a dolly assembly, a vertical beam having a first end connected to the dolly assembly and a second end connected to the tray, and a mechanism for altering the length of the vertical beam and maintaining the tray at a number of selectable distances from the dolly assembly. The chassis may also carry a power converter and a power unit including a rechargeable battery for supplying power to the device through the power converter while the device is supported within the docking station, and a battery charger connectable to an AC power source for charging the rechargeable battery. A power cord may connect the battery charger to the AC power source, and the power unit may include a power cord storage assembly operable for retracting the power cord when the power cord is not connected to the AC power source.

That the invention improves over the drawbacks of the prior art and how it accomplishes the advantages described above will become apparent from the following detailed description of the exemplary embodiments and the appended drawings and claims.

BRIEF DESCRIPTION OF THE DRAWINGS

FIG. 1 illustrates a mobile workstation including a docking station for a computer terminal in a typical environment, such as a patient's hospital room.

FIGS. 2A–2D are a series of side views of the mobile workstation of FIG. 1 illustrating the operation of an adjustable-height horizontal tray and a tiltable docking station.

FIGS. 3A–3D are a series of perspective views of the docking station forming part of the mobile workstation of FIG. 1 showing the push-down-and-tilt motion used to remove the wireless terminal from the docking station.

FIGS. 4A–4B are perspective views of the mobile workstation of FIG. 1 showing the operation of a pull-out keyboard tray.

FIG. 5A is a side view of the horizontal tray of the mobile workstation of FIG. 1 showing an access hole and a release lever for raising and lowering the horizontal tray.

FIG. 5B is a perspective view of the horizontal tray of the mobile workstation of FIG. 1 showing an access hole and a release lever for raising and lowering the horizontal tray.

FIG. 6A is a back view of the horizontal tray and mounting bracket of the mobile workstation of FIG. 1.

FIG. 6B is a reverse view of the mounting bracket of FIG. 6A.

FIG. 7A is an exploded view the mounting bracket of FIG. 6A and associated clutch assemblies.

FIG. 7B is a side view of a spring washer for the clutch assemblies.

FIG. 7C is a perspective view of the spring washer of FIG. 7B.

FIGS. 10A–10B are perspective views of the mobile workstation of FIG. 8 showing the operation of a pull-out keyboard tray.

FIG. 17 is a rear right side perspective view of the mobile workstation in FIG. 16.

DETAILED DESCRIPTION OF THE DISCLOSED EMBODIMENTS

Figure 8:
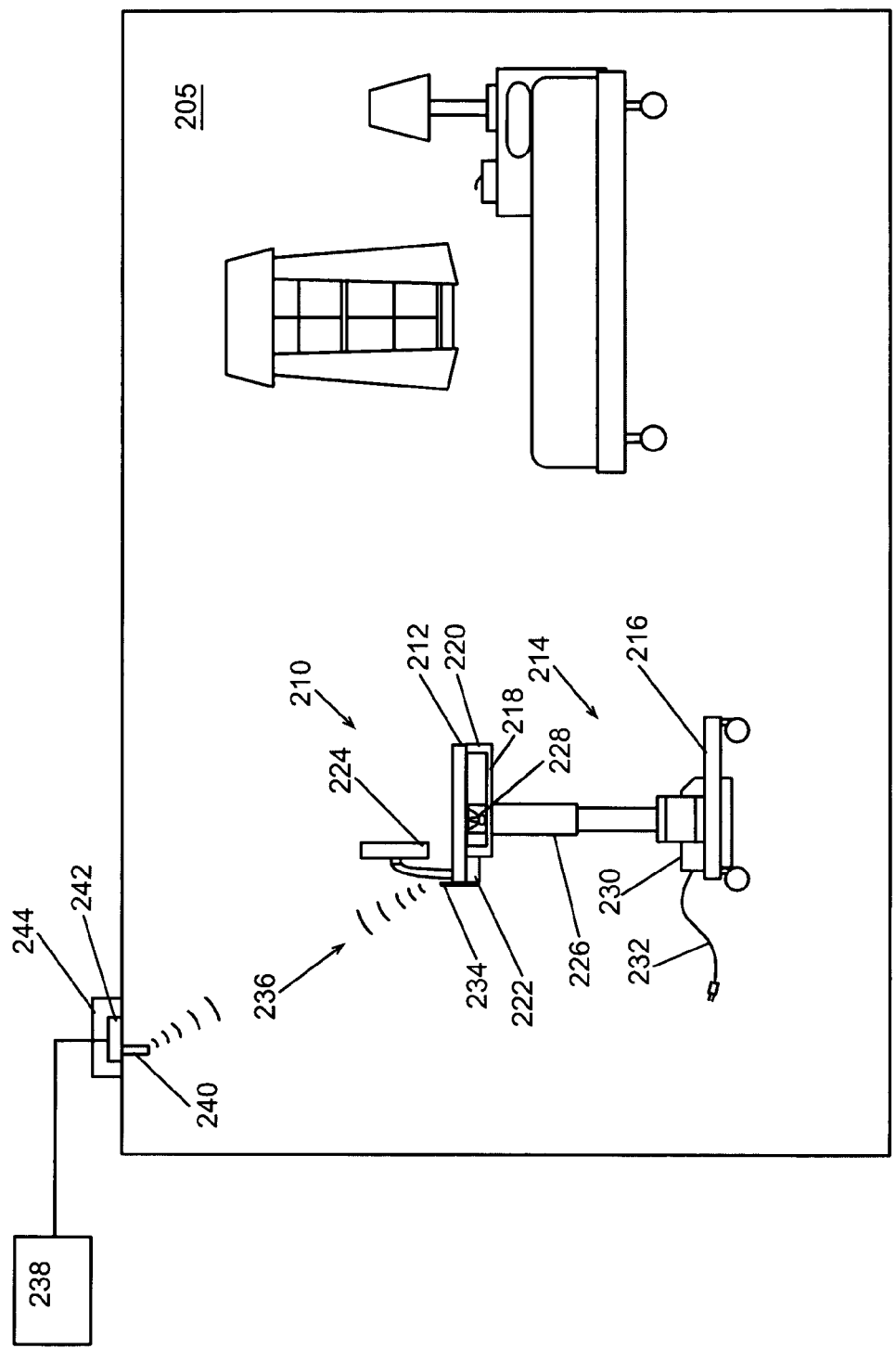
FIG. 8 illustrates a mobile workstation including a computer terminal and a display screen in a typical environment, such as a patient's hospital room.

The present invention may be embodied in a mobile workstation that includes an adjustable-height horizontal tray and a vertically-mounted docking station mounted to the horizontal tray. The docking station removably supports a computer terminal having a display screen, which may also serve as a touch-sensitive input device, that can be easily seen and accessed when the computer terminal is stored within the docking station. The mobile workstation also includes a keyboard located on a pull-out keyboard tray mounted to the underside of the horizontal tray. The keyboard is connected to the computer terminal by way of the docking station, so that the keyboard is automatically connected to the computer terminal whenever the terminal is stored within the docking station.

A tiltable bracket mounts the docking station to the horizontal tray. A clutch assembly allows the angle of the bracket, and along with it the angle of the docking station and the computer terminal, to be adjusted to avoid glare on the terminal's display screen. A spring-mounted, vertically-movable leveling tray allows the wireless terminal to be easily removed from the docking station using a push-down-and-tilt motion. An electronic lock selectively prevents vertical movement of the leveling tray to secure the computer terminal within the docking station. The docking station may also include a key-operated lock, which may be used to unlock the docking station in the event of a power outage or if the electronic lock should fail.

The mobile workstation also carries a power converter and a power unit including an extended-life battery, a battery charger that connects to an AC power supply to charge the conventional battery located inside the computer terminal as well as the extended-life battery carried on the mobile workstation. The power converter converts electrical power supplied by the battery to a suitable electrical input source for the computer terminal and the terminal display. The rechargeable battery power supply increases the battery life of the computer terminal to about 8–12 hours, which allows use of the computer terminal for an extended time before having to fully recharge it. The power unit includes two status-indicator lights to indicate when the unit is operating on AC power and when the battery is low, and a seven-level battery status-indicator light. The power unit may also include a sensor that indicates when the battery is low.

With the docking station configuration described above, a medical practitioner making the rounds can push the mobile workstation from room to room and use the same computer terminal when attending each patient. The extended-life battery allows the mobile workstation to be used for an entire shift before recharging. The mobile workstation thus eliminates the need for locating a wall-mounted cradle and associated computer terminal outside each patient's room. Because the docking station is vertically mounted, the computer terminal does not occupy the top surface of the horizontal tray, which allows this area to be used as a work surface. The leveling tray allows the computer terminal to be easily removed from, and replaced for storage within, the docking station with one hand. The electronic lock allows the docking station to be easily locked and unlocked with one hand.

Another embodiment of the present invention may be embodied in a mobile workstation that includes an adjustable-height horizontal tray on a chassis, a vertically mounted display screen mounted above the horizontal tray, a wireless computer terminal and a power converter mounted underneath the horizontal tray, a pull-out keyboard tray mounted beneath the wireless computer terminal, and a power unit mounted to the chassis. The horizontal tray includes an underside front mounting bracket to support the wireless computer terminal, and a rear mounting bracket to support the power converter. The front mounting bracket supports the wireless computer terminal adjacent to and beneath the horizontal tray, leaving the work surface of the horizontal tray available for other operator uses. The back mounting bracket or wiring tray supports the power converter adjacent to and beneath the horizontal tray so that the power converter easily connects to the wireless computer terminal. A tray housing mounted to the underside of the horizontal tray supports a pull-out keyboard tray so that a keyboard mounted within the pull-out tray does not interfere with the front mounting bracket or the rear mounting bracket. The keyboard communicates with the computer terminal through a conventional electrical connection so that the keyboard can be easily connected to the computer terminal whenever the wireless computer terminal is stored within the mobile workstation. The wireless computer terminal removably connects to the display screen that mounts to the top surface of the horizontal tray with a tiltable bracket.

The mobile workstation also carries a power unit including an extended-life battery and a battery charger that connects to an AC power supply to charge the conventional battery located inside or adjacent to the wireless computer terminal as well as the extended-life battery carried on the mobile workstation. Each battery connects to the power converter to supply power to the wireless computer terminal and the terminal display through the power converter. The rechargeable battery power supply increases the battery life of the computer terminal to about 8–12 hours, which allows use of the computer terminal for an extended time before having to fully recharge it. The power unit includes two status-indicator lights to indicate when the unit is operating on AC power and when the battery is low, and a seven-level battery status-indicator light. The power unit may also include a sensor that indicates when the battery is low.

Yet another embodiment of the present invention may include an adjustable-height horizontal tray on a chassis, a wireless computer terminal mounted above the horizontal tray, a display screen mounted above the wireless computer terminal, a pull-out keyboard tray mounted beneath the horizontal tray, and a power unit mounted to the chassis. The horizontal tray includes a mounting bracket to support the wireless computer terminal above the horizontal tray, leaving the part of the work surface of the horizontal tray available for other operator uses. A tray housing mounted to the underside of the horizontal tray supports a pull-out keyboard tray so that a keyboard mounted within the pull-out tray does not interfere with the bottom of the horizontal tray. The keyboard communicates with the computer terminal through a conventional electrical connection so that the keyboard can be easily connected to the computer terminal whenever the wireless computer terminal is stored within the mobile workstation. The wireless computer terminal removably connects to the display screen that mounts to the top surface of the horizontal tray with a tiltable bracket.

The mobile workstation also carries a power converter and a power unit including an extended-life battery and a battery charger that connects to an AC power supply to charge the conventional battery located inside or adjacent to the wireless computer terminal as well as the extended-life battery carried on the mobile workstation. Each battery connects to the power converter to supply power to the wireless computer terminal and the terminal display through the power converter. The rechargeable battery power supply increases the battery life of the computer terminal to about 8–12 hours, which allows use of the computer terminal for an extended time before having to fully recharge it. The power unit includes two status-indicator lights to indicate when the unit is operating on AC power and when the battery is low, and a seven-level battery status-indicator light. The power unit may also include a sensor that indicates when the battery is low.

With the wireless computer terminal configurations described above, a medical practitioner making the rounds can push the mobile workstation from room to room and use the same computer terminal when attending each patient. The extended-life battery allows the mobile workstation to be used for an entire shift before recharging. The mobile workstation thus eliminates the need for locating a wall-mounted cradle and associated computer terminal outside each patient's room. When the computer terminal is mounted beneath the horizontal tray, the computer terminal does not occupy the top surface of the horizontal tray, which allows this area to be used as a work surface. The front mounting bracket allows the computer terminal to be easily removed from, and replaced for storage within, the front mounting bracket. In the embodiment where the computer terminal is mounted above the horizontal tray, the computer terminal does not occupy the entire top surface of the horizontal tray, which allows the remaining area to be used as a work surface. In this configuration, the mounting bracket above the horizontal tray allows the computer terminal to be easily removed from, and replaced for storage within, the mounting bracket.

The wireless computer terminal in a mobile workstation can also communicate through a radio-frequency communication channel via a radio transmitter/receiver terminal antenna attached to the top of the horizontal tray. In this manner, the wireless computer terminal can exchange information with a computer network, such as a distributed patient-care computer network.

Those skilled in the art will appreciate that the mobile workstation could be configured to support a device other than a docking station or a wireless computer terminal, such as a medical instrument. For example, the mobile workstation could be configured to support an ultra-sound device used to view a fetus. The docking station or the wireless computer terminal could be removed from the mobile workstation, and a similarly sized ultra-sound device could be placed within the mobile workstation. The patient could then view the display screen of the mobile workstation to see the results of the ultra-scan procedure. Many other applications, both medical and non-medical, will become apparent to those skilled in the art from the examples described in this specification.

Turning now to the drawings, in which like numerals indicate like elements throughout the several figures, FIG. 1 illustrates a mobile workstation 10 in a typical environment, such as a patient's hospital room 5. The mobile workstation 10 includes an adjustable-height horizontal tray 12 supported by a chassis 14. The chassis 14 includes a dolly assembly 16 that allows an operator, such as a medical practitioner, to easily push the mobile workstation 10 from place to place. The horizontal tray 12 supports a docking station 18 that, in turn, removably supports a device, such as the wireless computer terminal 20 with a terminal display screen. The chassis 14 includes a vertical beam 22 connecting the horizontal tray 12 to the dolly assembly 16.

The vertical beam 22 includes a gas-spring height adjustment mechanism for adjusting the length of the beam and, thus, the height of the horizontal tray 12 above the dolly assembly 14. For example, the chassis 14 may be a model MPC2001 manufactured by JACO, Inc. with the standard tray replaced by the horizontal tray 12 shown in FIG. 1. Those skilled in the art will appreciate that other types of wheeled chassis would be suitable for this purpose. In addition, other types of height adjustment mechanisms would also be suitable, such as a rack and pinion mechanism, a cable and pulley mechanism, a ratchet mechanism, a ball screw mechanism, a removable pin and holes arrangement, and so forth. Nevertheless, a gas-spring height adjustment mechanism is preferred because it is easy operate and ergonomically desirable.

The mobile workstation 10 also carries a power unit 24 including a power converter, a battery charger, an extended-life battery, a power cord 26, and a recoil mechanism that automatically recoils the power cord when the cord is not plugged into an AC outlet. The power converter converts power received from the power unit 24 to suitable power for the wireless computer terminal 20. The power unit 24 is located on the lower end of the chassis 14. For example, the power unit 24 may reside between two metal beams in the dolly assembly 16 at the lower end of the chassis 14. The extended-life battery may be a 12-Volt sealed lead acid battery, and the power supply may be a 120-Volt AC to 16-Volt DC converter.

The power unit 24 typically includes a first status-indicator light to inform the user when the unit is running on AC power, a second status-indicator light to inform the user when the battery needs recharging, and a seven-level battery status-indicator light to inform the user about the power status of the battery. The power unit 24 may also include an alarm or audible indicator to inform the user when the extended-life battery power needs recharging. The extended-life battery can be recharged by connecting the plugging the power cord 26 into a standard 120-volt AC outlet. When not in use, the recoil mechanism retracts the power cord 26 into the power unit 24.

The wireless computer terminal 20 typically includes a radio transmitter/receiver antenna for communicating over an approved radio frequency. In particular, the wireless computer terminal 20 may establish a radio-frequency communication channel 28 with a distributed patient-care computer network 30 through an antenna 32 connected to a network access point 34. This network access point is typically located in an enclosure 36 located above the ceiling of the hospital room. The network access point 34, in turn, allows the wireless computer terminal 20 to communicate with the distributed patient-care computer network 30. For example, the network access point 34 may be a RANGE-LAN2 7500 Series Access Point manufactured by PROXIM, INC. of Mountain View, Calif.

FIGS. 2A–2D are a series of side views of the mobile workstation 10 illustrating the operation of an adjustable-height horizontal tray 12 and the tiltable docking station 18. FIG. 2A shows the mobile workstation 10 with the height-adjustable horizontal tray 12 in a vertically lowered position. To raise the tray, the operator places his or her hand through an opening 40 in the side of the horizontal tray 12. The operator then lifts a release lever 42, which releases a stop in the gas-spring height adjustment mechanism in the vertical beam. The operator then raises or lowers the horizontal tray 12 while holding the release lever 42 in a raised position.

Assistance provided by the gas-spring height adjustment mechanism allows the operator to change the height of the horizontal tray 12 with little effort. Once the horizontal tray 12 is at a desired height, represented by the height shown in FIG. 2B, the operator releases the lever 42, which locks the tray at the desired height. With this type of mechanism, the operator can quickly and easily place the horizontal tray 12 at virtually any height within the adjustment range of the gas-spring height adjustment mechanism. The assistance provided by the gas-spring height adjustment is ergonomically desirable in that it avoids back strain or other lifting problems that could otherwise be encountered by operators using the mobile workstation 10.

FIG. 2C illustrates the mobile workstation 10 with the docking station 18 in a vertical position. A tiltable bracket 44 attaches the docking station 18 to the horizontal tray 12. A clutch 46 in the tiltable bracket maintains the docking station 18 in a number of selectable rotational positions relative to the tray 12. The rotational range of the tiltable bracket 44 is preferably about 30 degrees rearward from vertical. That is, the tiltable bracket 44 preferably allows the docking station 18 to be rotated from the position shown in FIG. 2C to the position shown in FIG. 2D. The tiltable bracket 44 could also be configured to allow the docking station 18 to rotate forward through a similar rotational range.

It should be understood that the term "substantially vertical" may include a range about a strictly vertical orientation, represented by the 30 degree range illustrated by FIGS. 2C–D. For example, the term "substantially vertical" includes configurations in which the bracket 44 maintains the docking station 18 in a strictly vertical orientation, or at a fixed rotational orientation with a vertical component, or within a range of rotational orientations including orientations that include vertical components. Alternatively, the docking station 18 could be supported in a substantially horizontal position, for example by a drawer or pull-out tray located above or under the horizontal tray 12. Other locations for the docking station 18 may be preferred in certain environments. For example, the docking station could be mounted to the side of the horizontal tray 12, to the underside of the horizontal tray 12, to the dolly assembly 16, to the vertical beam 22, and so forth.

The clutch 46 imparts sufficient rotational resistance to maintain the docking station 18, with an associated computer terminal 20, at any of the rotational aspects within the rotational range defined by the tiltable bracket 44. At the same time, the rotational resistance imparted by the clutch 46 is pliant enough to allow the operator to change the rotational orientation of the docking station 18 with one hand. For example, the operator may easily adjust the angle of the docking station 18 to avoid glare on the display screen of the computer terminal 20. The tiltable bracket 44 and the clutch 46 are described in greater detail with reference to FIGS. 6A–B and 7A–C below.

FIGS. 3A–3D are a series of perspective views of the docking station 18 and an associated wireless computer terminal 20 showing the push-down-and-tilt motion used to remove the terminal from the docking station. The docking station 20 includes a base 50, a back plane 52, and two spaced-apart retaining arms 54 and 56. When the computer terminal 20 is located in the docking station, the retaining arms 54 and 56 support the top side 62 of the terminal. The base 0.50 includes a leveling tray 58 with a rubber cushion 60 for receiving the bottom side of the computer terminal 20. The rubber cushion 60 includes raised collars on either end that prevent the computer terminal 20 from being removed from the docking station 18 when the leveling tray 58 is locked in the upper position, as shown in FIG. 3A.

The docking station 18 includes a control panel 62 having a keypad 64, typically with four keys. The docking station 18 may be configured so that the keypad 64 operates as an electronic combination lock. The leveling tray 58 can be depressed when the docking station is unlocked and, when the docking station 18 is locked, the leveling tray 58 cannot be depressed. The docking station 18 may also include a manual key lock that may be used to lock and unlock the docking station in the event of a power outage or a malfunction of the electronic lock.

The control panel 62 may also include status lights 64a-c that indicate status information regarding the docking station 18. For example, these status lights typically indicate whether the docking station is locked, whether power is on, and provide status information while a user is configuring the docking station with passwords. A touch-pin battery charging terminal 68 or other conventional electrical connection located in the leveling tray 58 may be used to charge a battery within the computer terminal 20 while the terminal is stored within the docking station 18. This battery charging terminal, in turn, is connected to the power unit 24. The power unit includes the power cord 26, which may be plugged into a standard 120 Volt AC outlet. In addition, the docking station 18 may include a communication interface, such as an optical interface, for communicating data between the computer terminal 20 and the docking station 18 while the terminal is stored within the docking station. This allows the computer terminal 20 to communicate with the keypad 64 and/or an optional keyboard that plugs into the docking station 18.

To remove the computer terminal 20, an operator first unlocks the docking station 18 and then places his or her hand on the top side 62 of the terminal and pushes downward. Provided that the docking station 18 is unlocked, this motion depresses the leveling tray 58, as shown in FIG. 3B. The operator then tilts the terminal 20 forward, as shown in FIG. 3C, and removes the terminal 20, as shown in FIG. 3D. An example of a suitable docking station is described in commonly owned U.S. patent application Ser. No. 08/841, 496, entitled "Cradle For Holding A Device," filed Apr. 23, 1997, which is incorporated into this specification by reference.

FIGS. 4A–B are perspective views of the mobile workstation 0.10 showing the operation of a pull-out keyboard tray 70, which is supported by the underside of the horizontal tray 12. The pull-out keyboard tray 70 slides from an inner position, shown in FIG. 4A, to an outer position, shown in FIG. 4B. A keyboard mounted on the keyboard tray 70 typically plugs into the docking station 18, which communicates keystrokes with the computer terminal 20 by way of a conventional electrical connection. This allows an operator to easily remove the computer terminal 20 from the docking station 18.

In FIGS. 4A–4B, the top portion of a rectangular cover for the vertical beam 22 has been removed, showing an underlying shaft 72 and a power cable 73, connecting the power unit 24 to the docking station 18. This shaft 72 connects to the gas-spring height adjustment mechanism 74 that allows adjustment of the height of the horizontal tray 12. The gas-spring height adjustment mechanism 74, which is located at the bottom of the vertical beam 22, sits on top of the dolly assembly 16. This dolly assembly includes an arched cross-beam 76 that connects to two horizontal runner beams 78a–b. Two casters, represented by the caster 80, are connected to the bottom sides of each horizontal runner beam 78a–b. The power unit 24 is mounted below the arched cross beam 76 to an arched support plate 82, which connects between the horizontal runner beams 78a–b.

FIGS. 4A–B also show that the top side of the horizontal tray 12 defines a substantially horizontal work surface 86, which is bordered by a raised edge guard 88. The rear edge of the horizontal tray 12 includes a recess 90 for the docking station 18, which defines an elongate dimension 92 and a relatively slender dimension 94. That is, the docking station 18 is substantially taller than it is thick. The tiltable mounting bracket 44 supports the docking station 18 so that the elongate dimension 92 is substantially vertical and the relatively slender dimension 94 is substantially horizontal. Because the docking station 18 is vertically mounted, the terminal 20 does not occupy the top surface 86 of the horizontal tray 12, which allows this area to be used as a work surface. In addition, the computer terminal 20 typically includes a display screen 96, and the docking station 18 supports the terminal with the display screen substantially perpendicular to and above the top surface 86 of the horizontal tray 12 for easy viewing. It will be understood that the term "substantially perpendicular" includes a range of orientations because the docking station 18 may rotate through a rotational range about a strictly perpendicular orientation.

FIG. 5A is a side view of the horizontal tray 12 showing the access hole 40 and the release lever 42 for raising and lowering the horizontal tray 12. The release lever 42 operates the gas-spring height adjustment lever, which is shown best in FIG. 4A. FIG. 5A also shows the end of the pull-out keyboard tray 70, which includes a lip 98 to aid in pulling the keyboard tray out and pushing it back in.

FIG. 5B is a perspective view of the horizontal tray 12 showing the access hole 40 and the release lever 42 for raising and lowering the horizontal tray 12. FIG. 5B also shows the top surface 86, the edge guard 88, and the recess 90 of the horizontal tray 12. The top surface 86 of the horizontal tray 12 is preferably constructed from a non-porous material, such as plastic or metal. For example, the horizontal tray 12 may be constructed from a flat wooden, particle board, or composite substrate covered with a plastic overlay defining the top surface 86 and the edge guard 88. The plastic overlay may be created with an injection mold, and then glued to the substrate. The bracket 44 includes mounting brackets 102a–b and a back plane 100 supporting the docking station. The back plane 100 may be formed from a heavy gauge sheet metal, fiberglass, or composite. The sides 103 and bottom 104 the horizontal tray 12 may be formed from sheet metal.

FIG. 6A is a back view, and FIG. 6B is a reverse view, of the horizontal tray 12 showing the tiltable bracket 44, including the back plane 100 and mounting brackets 102a–b. The mounting brackets 102a–b are bolted to the rear side of the horizontal tray 12 and extend into the recess 90 so that the back plane 100 is approximately flush with the rear side of the horizontal tray 12 when the back plane is in a vertical position. The mounting brackets 102a–b each include an arcuate slot 106a–b to allow the back plane 100 to rotate through a rotational range with respect to the mounting brackets. For example, that rotational range is approximately 30 degrees in the configuration shown in FIGS. 6A–B. Clutch assemblies 46a–b at the connections between the mounting brackets 102a–b the back plane 100 support the back plane 100, with an associated docking station 18 and computer terminal 20, in virtually any rotational orientation within the rotational range defined by the slots 106a–b.

FIG. 7A is an exploded view the mounting brackets 102a–b and the clutch assemblies 46a–b. Referring to the clutch assembly 46b for illustration purposes, this assembly includes two identical connection assemblies 110a–b. Referring now to the connection assembly 110a for illustration purposes, this assembly includes a threaded standoff 112 including a collar that passes through a hole in the support frame 114 of the back plane 100 and a rim that catches on the support frame. The threaded standoff 112 is preferably press-fitted into the hole in the support frame 114.

The connection assembly 110a also includes a nylon shoulder washer 116 including a collar that passes through a hole in the mounting bracket 44b and a rim that catches on the mounting bracket. The collar of nylon shoulder washer 116 is sized to snugly receive the threaded standoff 112. The connection assembly 110a also includes a nylon washer 118, two steel washers 120 and 122, and a steel spring washer 124 positioned for compression between the steel washers. A bolt 126 passes through these washers and screws into the threaded standoff 112. The bolt 126 may be tightened into the threaded standoff 112 to compress the steel spring washer 124 and provide a desired amount of resistance in the connection assembly 110a.

FIG. 7B is a side view of the spring washer 124, and FIG. 7C is a perspective view of the spring washer. These figures show that the spring washer 124 has a slight conical shape that is raised in the middle with respect to the outer perimeter. This type of spring washer provides a compact and inexpensive mechanism for imparting an adjustable amount of resistance in the connection assembly 110a. Those skilled in the art will appreciate that other types of clutch assemblies could be employed in embodiments of the invention.

Another embodiment of a mobile workstation is shown in FIG. 8 illustrates a mobile workstation 210 in a typical environment, such as a patient's hospital room 205. The mobile workstation 210 includes an adjustable-height horizontal tray 212 supported by a chassis 214. The chassis 214 includes a dolly assembly 216 that allows an operator, such as a medical practitioner, to easily push the mobile workstation 210 from place to place. The horizontal tray 212 includes an underside tray housing 218, an underside front mounting bracket 220, and an underside back mounting bracket 222 or wiring tray.

The tray housing 218 supports a keyboard (not shown) or keypad for a wireless computer terminal (not shown). The wireless computer terminal mounts within the front mounting bracket 220. The back mounting bracket 222 or wiring tray supports a power converter (not shown) supplying power to the wireless computer terminal. A tiltable display screen 224 attaches to the top of the horizontal tray 212 while connecting to the wireless computer terminal. The back mounting bracket 222 or wiring tray can also support additional power converters for the display screen 224 or for other electrical devices associated with the mobile workstation 210.

The chassis 214 includes a vertical beam 226 connecting the horizontal tray 212 to the dolly assembly 216. The vertical beam 226 includes a gas-spring height adjustment mechanism (not shown) and a release lever 228 for adjusting the length of the beam 226 and, thus, the height of the horizontal tray 212 above the dolly assembly 216. For example, the chassis 214 may be a model MPC2001 manufactured by JACO, Inc. with the standard tray replaced by the horizontal tray 212 shown in FIG. 8. Those skilled in the art will appreciate that other types of wheeled chassis would be suitable for this purpose. In addition, other types of height adjustment mechanisms would also be suitable, such as a rack and pinion mechanism, a cable and pulley mechanism, a ratchet mechanism, a ball screw mechanism, a removable pin and holes arrangement, and so forth. Nevertheless, a gas-spring height adjustment mechanism 228 is preferred because it is easy operate and ergonomically desirable.

The mobile workstation 210 also carries a power converter (not shown) within the back mounting bracket 222 and a power unit 230 including a battery charger, an extended-life battery, a power cord 232, and a recoil mechanism that can retract the power cord when the cord is not in use. The power unit 230 supplies power to the wireless computer terminal through the power converter. The power unit 230 is located on the lower end of the chassis 214. For example, the power unit 230 may reside between two metal beams in the dolly assembly 216 at the lower end of the chassis 214. A suitable power unit 230 is a 26. Amp-Hour battery providing a regulated 10–16 Volt output at 40 watts with an automatic low power cut-off. The extended-life battery may be a 12-Volt sealed lead acid battery, and the battery charger may be a 120-Volt AC to 16-Volt DC converter.

The power unit 230 typically includes a first status-indicator light to inform the user when the unit is operating off of AC power, a second status-indicator light to inform the user when the battery needs recharging, and a seven-level battery status-indicator light. The power unit 230 may also include a sound indicator that beeps to inform the user when the extended-life battery needs recharging. When plugged into an AC outlet, the battery charger will charge both the extended-life battery and operate the wireless computer terminal by supplying the power converter connected to the computer terminal. The extended-life battery can be recharged by plugging the power cord 232 into a standard 120-volt AC outlet. When not in use, the recoil mechanism can retract the power cord 232 into the power unit 230.

The wireless computer terminal inside the mobile workstation 210 communicates through a radio transmitter/receiver terminal antenna 234 attached to the top of the horizontal tray 212. The terminal antenna 234 is operable for communicating over an approved radio frequency. A suitable radio transmitter/receiver to mount to the wireless computer terminal is a Lucent. Extended 802.11 radio with a cable for using an external antenna. A suitable terminal antenna 234 for mounting to the horizontal tray 212 is a whip antenna used in DOS VMT products (1380/1390, 1320/1330). In particular, the wireless computer terminal may establish a radio-frequency communication channel 236 with a distributed patient-care computer network 238 through an antenna 240 connected to a network access point 242. This network access point 242 is typically located in an enclosure 244 located above the ceiling, of the hospital room. The network access point 242, in turn, allows the wireless computer terminal to communicate with the distributed patient-care computer network 238. For example, the network access point 242 may be a RANGELAN2 7500. Series Access Point manufactured by PROXIM, INC. of Mountain View, Calif.

Figure 9D:
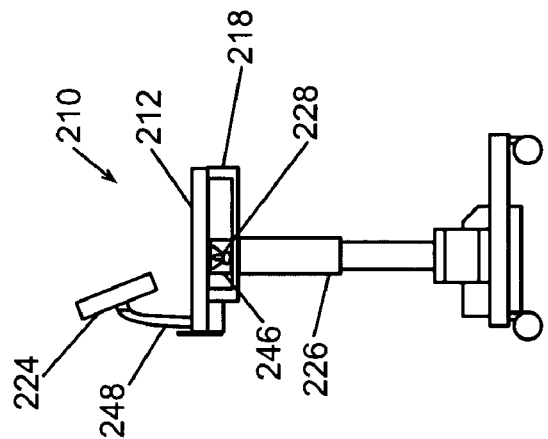
FIGS. 9A–9D are a series of side views of the mobile workstation of FIG. 8 illustrating the operation of an adjustable-height horizontal tray and a tiltable display screen.
Figure 9C:
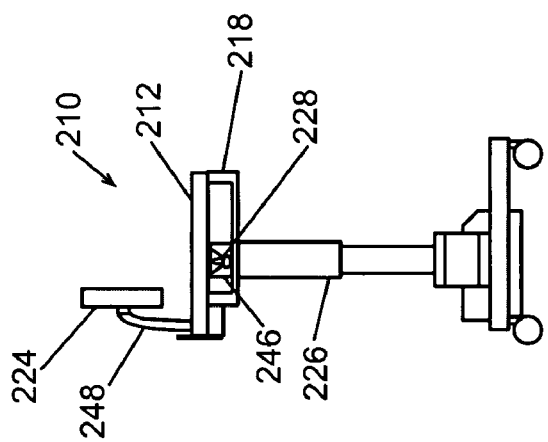
Figure 9B:
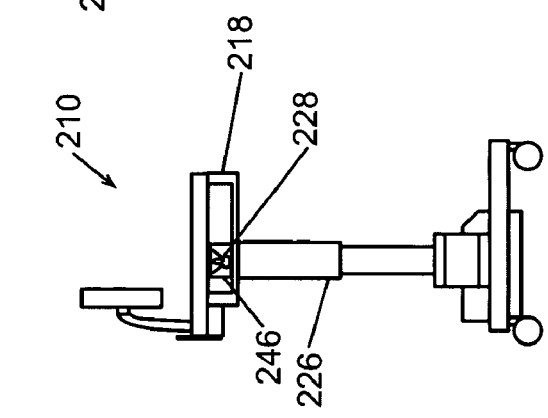
Figure 9A:
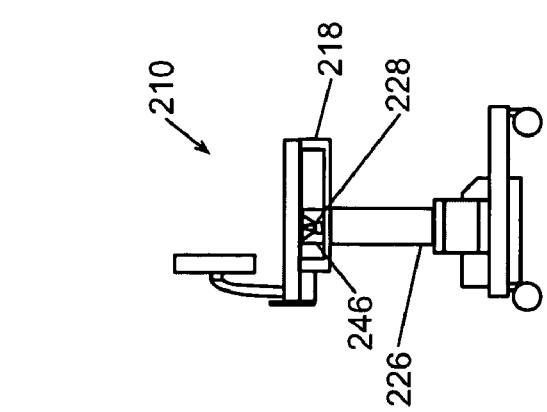

FIGS. 9A–9D are a series of side views of the mobile workstation 210 illustrating the operation of an adjustable-height horizontal tray 212 and the display screen 224. FIG. 9A shows the mobile workstation 210 with the height-adjustable horizontal tray 212 in a vertically lowered position. To raise the tray 212, the operator places his or her hand through an access opening 246 in the side of the tray housing 218. The operator then lifts the release lever 228, which releases a stop in the gas-spring height adjustment mechanism (not shown) in the vertical beam 226. The operator then raises or lowers the horizontal tray 212 while holding the release lever 228 in a raised position.

Assistance provided by the gas-spring height adjustment mechanism allows the operator to change the height of the horizontal tray 212 with little effort. Once the horizontal tray 212 is at a desired height, represented by the height shown in FIG. 9B, the operator releases the lever 228, which locks the tray 212 at the desired height. With this type of mechanism, the operator can quickly and easily place the horizontal tray 212 at virtually any height within the adjustment range of the gas-spring height adjustment mechanism. The assistance provided by the gas-spring height adjustment is ergonomically desirable in that it avoids back strain or other lifting problems that could otherwise be encountered by operators using the mobile workstation 210.

FIG. 9C illustrates the mobile workstation 210 with the display screen 224 in a vertical position. A tiltable bracket 248 attaches the display screen 224 to the horizontal tray 212. The tiltable bracket 248 maintains the display screen 224 in a number of selectable rotational positions relative to the tray 212 so that the display screen 224 is in front of users for ease of visibility. The rotational range of the tiltable bracket 248 is preferably about 30 degrees rearward from vertical. That is, the tiltable bracket 248 preferably allows the display screen 224 to be rotated from the position shown in FIG. 9C to the position shown in FIG. 9D. The tiltable bracket 248 could also be configured to allow the display screen 224 to rotate forward through a similar rotational range.

It should be understood that the term "substantially vertical" may include a range about a strictly vertical orientation, represented by the 30 degree range illustrated by FIGS. 9C–9D. For example, the term "substantially vertical"includes configurations in which the bracket 248 maintains the display screen 224 in a strictly vertical orientation, or at a fixed rotational orientation with a vertical component, or within a range of rotational orientations including orientations that include vertical components. Alternatively, the display screen 224 could be supported in a substantially horizontal position, for example by a drawer or pull-out tray located above or under the horizontal tray 212. Other locations for the display screen 224 may be preferred in certain environments. For example, the display screen 224 could be mounted to the side of the horizontal tray 212, to the underside of the horizontal tray 212, to the dolly assembly 216, to the vertical beam 226, and so forth.

The tiltable bracket 248 imparts sufficient rotational resistance to maintain the display screen 224, with an associated computer terminal (not shown), at any of the rotational aspects within the rotational range defined by the tiltable bracket 248. At the same time, the rotational resistance imparted by the tiltable bracket 248 is pliant enough to allow the operator to change the rotational orientation of the display screen 224 with one hand. For example, the operator may easily adjust the angle of the display screen 224 to avoid glare on the display screen 224. A clutch mechanism similar to that discussed with reference to FIG. 7 may be used to allow selective rotation of the display screen 224.

FIGS. 10A–10B are perspective views of the mobile workstation 210 showing the operation of a pull-out keyboard tray 250, which is supported by the tray housing 218 attached to the underside of the horizontal tray 212. The pull-out keyboard tray 250 slides from an inner position, shown in FIG. 10A, to an outer position, shown in FIG. 10B, along conventional rollers (not shown) within a conventional roller guide slots (not shown). Typically, rollers mounted to the bottom side of the keyboard tray 250 fit within roller guide slots attached to the top side of the tray housing 218. A keyboard (not shown) fits within the pull-out keyboard tray 250. The pull-out keyboard tray 250 is to detent when fully extended away from the front edge of the tray housing 218, permitting the operator to type on the keyboard without the keyboard tray 250 sliding back into the tray housing 218. When the pull-out keyboard tray 250 is in the retracted position, the keyboard tray 250 will not slide out during movement or transport of the mobile workstation 210.

As shown in FIG. 10B, the pull-out keyboard tray 250 can be extended outward from the front end of the tray housing 218. The rollers on the bottom of the pull-out keyboard tray 250 permit the pull-out tray 250 to roll forward within the roller guide slots along the length of the top side of the tray housing 218. The roller guide slots have a physical stop at the front end of the tray housing 218. When a roller makes contact with the physical stop at the front end of the tray housing 218, the pull-out keyboard tray 250 cannot be extended any further from the front edge of the tray housing 218.

In FIGS. 10A–10B, the top portion of a rectangular cover for the vertical beam 226 has been removed, showing an underlying shaft 252 and a power cable 254 connecting the power unit 230 to the power converter (not shown). This shaft 252 connects to the gas-spring height adjustment mechanism 256 that allows adjustment of the height of the horizontal tray 212. The gas-spring height adjustment mechanism 256, which is located at the bottom of the vertical beam 226, sits on top of the dolly assembly 216. This dolly assembly includes an arched cross-beam 258 that connects to two horizontal runner beams 260a–b. Two casters, represented by the caster 262, are connected to the bottom sides of each horizontal runner beam 260a–b. For example, a suitable size caster is a conventional 5" caster. The power unit 230 is mounted below the arched cross beam 258 with a support bracket 264, which connects between the horizontal runner beams 260a–b.

FIGS. 10A–10B also show that the top side 266 of the horizontal tray 212 defines a substantially horizontal work surface. The tiltable bracket 248 supports the display screen 224 so that the elongate dimension 268 is substantially vertical and the relatively slender dimension 270 is substantially horizontal. Because the display screen 224 is vertically mounted, the display screen 224 does not occupy a substantial portion of the top surface 266 of the horizontal tray 212, which allows this area to be used as a work surface. It will be understood that the term "substantially vertical" includes a range of orientations because the display screen 224 may rotate through a rotational range about a strictly perpendicular orientation.

FIG. 11A is a side view of the horizontal tray 212 and the attached tray housing 218 showing the access opening 246 and the release lever 228 for raising and lowering the horizontal tray 212. The release lever 228 operates the gas-spring height adjustment mechanism 256 previously shown in FIGS. 10A–10B. The access opening 246 in the side wall of the tray housing 218 provides convenient operator access to actuate the release lever 228.

Figure 11B:
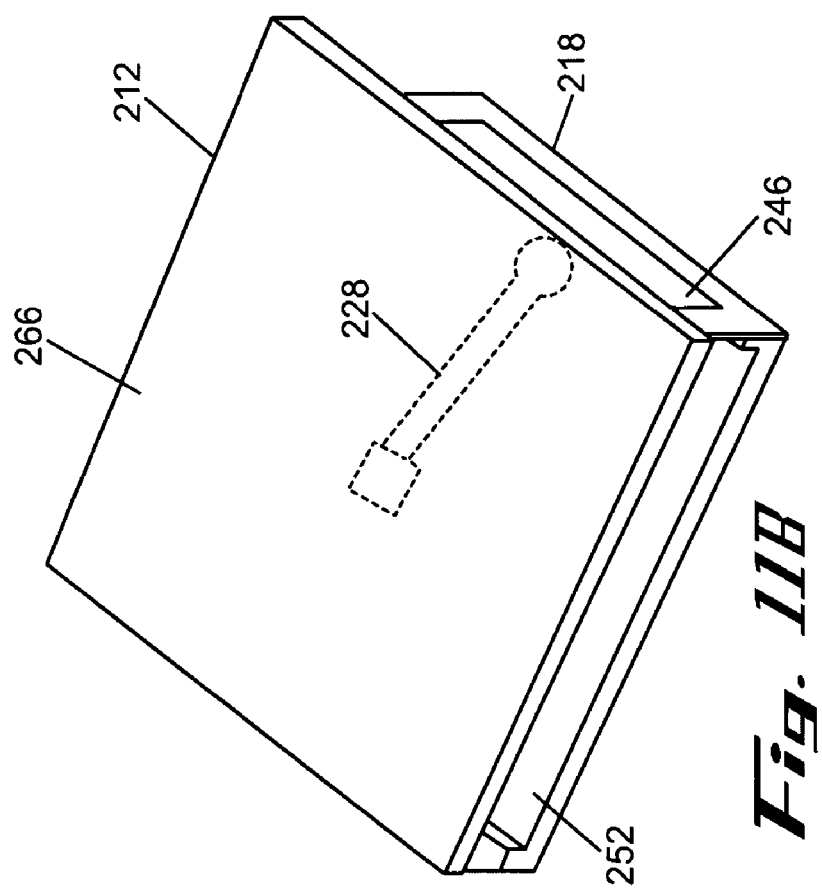
FIG. 11B is a perspective view of the horizontal tray of the mobile workstation of FIG. 8 showing an access opening and a release lever for raising and lowering the horizontal tray.
Figure 11H:
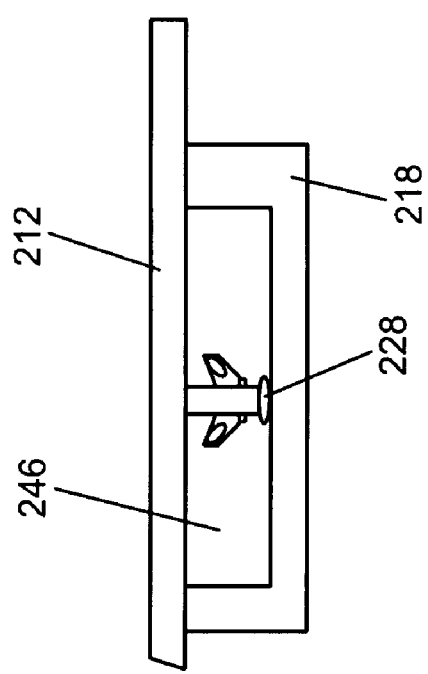
FIG. 11A is a side view of the horizontal tray of the mobile workstation of FIG. 8 showing an access opening and a release lever for raising and lowering the horizontal tray.

FIG. 11B is a perspective view of the horizontal tray 212 showing the access opening 246 and the release lever 228 for raising and lowering the horizontal tray 212. Typically, the release lever 228 has a tee or a paddle on the end, so that an operator can conveniently actuate the release lever 228 thereby raising or lowering the gas-spring height adjustment mechanism 256.

FIG. 11B also shows the top surface 266 of the horizontal tray 212. The top surface 266 of the horizontal tray 212 is preferably constructed from a non-porous material, such as plastic or metal. For example, the horizontal tray 212 may be constructed from a flat wooden, particle board, or composite substrate covered with a plastic overlay defining the top surface 266. The plastic overlay may be created with an injection mold, and then glued to the substrate. Those skilled in the art will appreciate that other types of horizontal trays could be employed in embodiments of the invention.

Figure 12C:
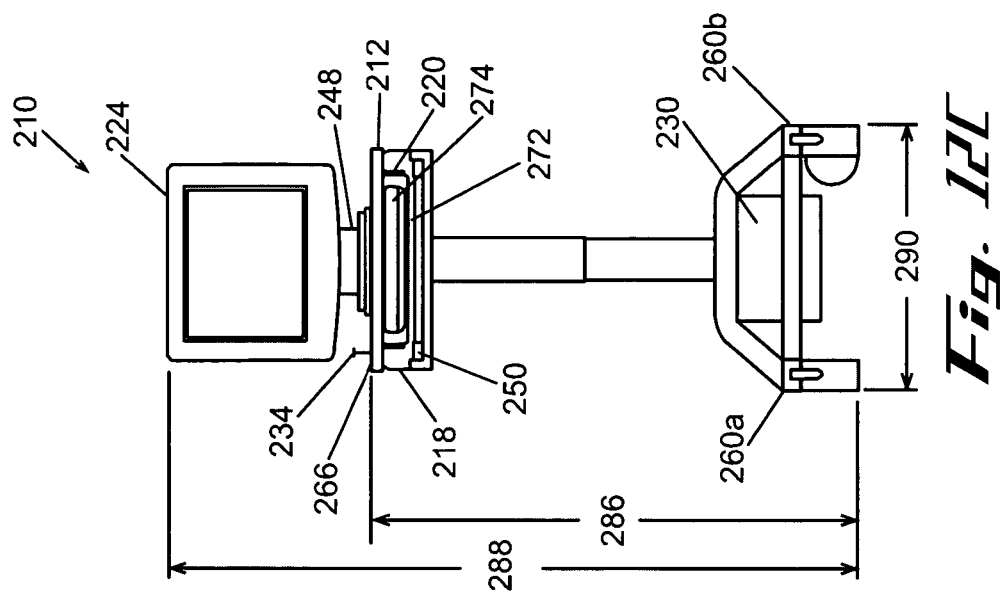
FIG. 12C is a front view of the mobile workstation of FIG. 8 showing the installation of the wireless computer terminal and the keyboard.
Figure 12B:
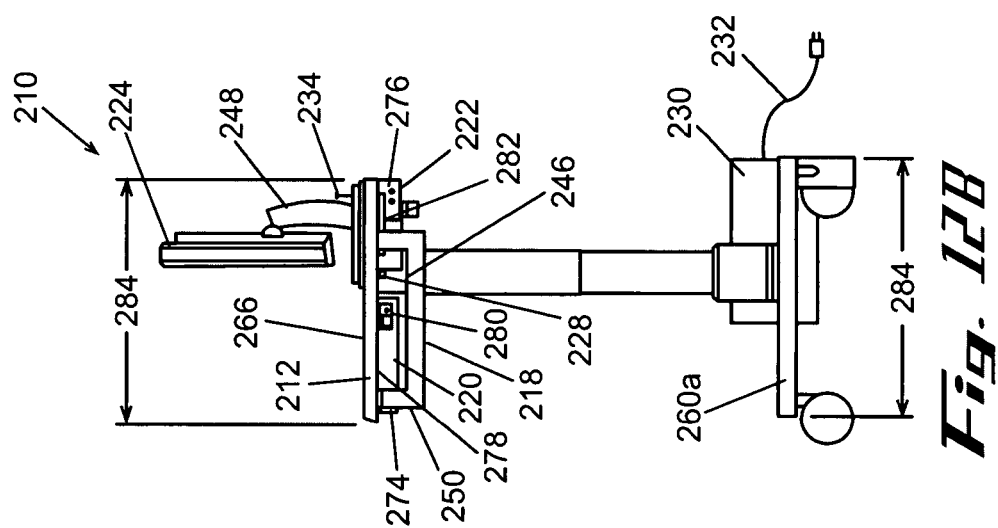
FIG. 12B is a side view of the mobile workstation of FIG. 8 showing the installation of the wireless computer terminal, keyboard, and battery pack.
Figure 12H:
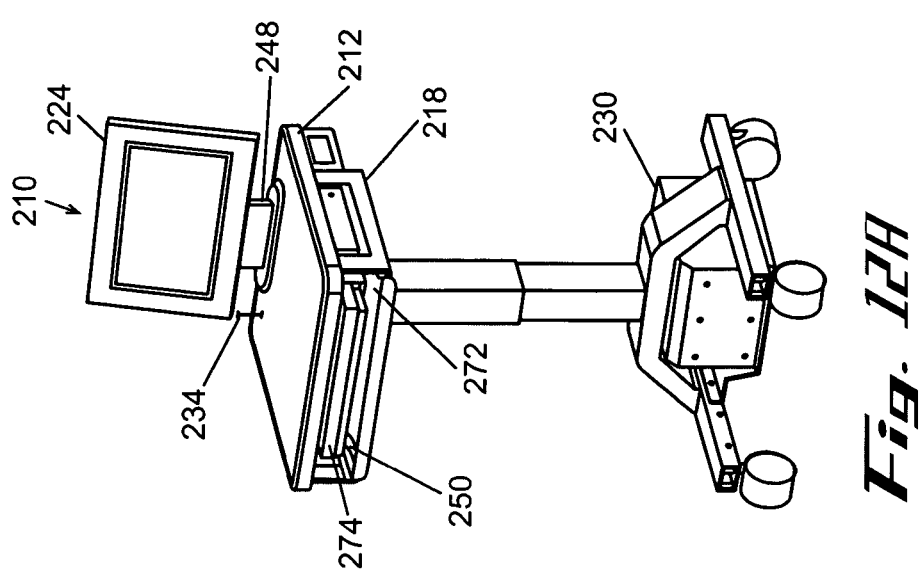
FIG. 12A is a perspective view of the mobile workstation of FIG. 8 showing the installation of the wireless computer terminal and the keyboard.

FIGS. 12A–12C are a series of detailed views of the mobile workstation 210 of FIG. 8, with the display screen 224, a keyboard 272, a wireless computer terminal 274, and a power unit 230. FIG. 12A is a perspective view of the mobile workstation 210 illustrated in FIG. 8. FIG. 12B is a side view of the mobile workstation 210 illustrated in FIG. 12A. FIG. 12C is a front view of the mobile workstation 210 illustrated in FIG. 12A.

In FIG. 12A, the mobile workstation 210 is shown with a display screen 224 mounted to the top surface of the horizontal tray 212. A tiltable bracket 248 connects the display screen 224 to the top of the horizontal tray 212. Conventional electrical connections (not shown) provide an interface between the wireless computer terminal 274 and the display screen 224. A suitable display screen 224 is a flat panel LCD with a 14–15" TFT viewable screen, a minimum video resolution of 1024×768 pixels, a minimum 200 nit, and a DC power input. Those skilled in the art will appreciate that other types of display screens could be employed in embodiments of the invention, including those having touch performance screens.

As shown in FIG. 12B, a front mounting bracket 220 mounts to the bottom side 278 of the horizontal tray 212, and holds the computer terminal 274 substantially parallel to the bottom side 278 of the front portion of the horizontal tray 212. The front mounting bracket 220 is sized to support the wireless computer terminal 274, such as a laptop computer, within the front bracket 220 and adjacent to the bottom side of the horizontal tray 212. The front mounting bracket 220 has an access window 280 in the side wall for operator access to various ports or interfaces in the side of the wireless computer terminal 274.

The wireless computer terminal 274 may include a communication interface, such as an optical interface or a conventional electrical connection, for communicating data between the computer terminal 274 and the keyboard 272. The communication interface between the keyboard 272 and the computer terminal 274 allow the keyboard 272 to communicate keystrokes to the computer terminal. 274. This type of operation permits an operator to easily remove the computer terminal 274 from the front mounting bracket 220, or to remove the keyboard 272 from the keyboard tray 250. As previously described in FIG. 8, the wireless computer terminal 274 can then send signals through the terminal antenna 234 attached to the top surface 266 of the horizontal tray 212 to communicate with a remote computer network (shown in FIG. 8 as 238) via a radio frequency communication channel (shown in FIG. 8 as 236).

A suitable wireless computer terminal is an Orion PC manufactured by Netier Technologies. The variety of computer terminal models offered under the Orion PC family includes a "Thin Client" configuration, or a "Fat" system. For example, the "Fat" system comprises an ACD-MSX-100 base unit with a Pentium 266 MHz microprocessor on a Socket 7 motherboard operating a MICROSOFT Windows 95 operating system, 32–128 MB RAM, 2 MB Video RAM, 2 GB hard disk, two Type II PCMCIA slots, one Type III PCMCIA slot, one parallel port, one serial port, one video port, one LCD port, dual USB ports, one PS/2 keyboard/mouse port, one IrDa port, and one battery module. Optional accessories for the Orion PC family include an automobile cigarette lighter charger/adaptor, and AC charger/adaptor, a second battery module, a floppy disk drive, and a CD-ROM or CD-R drive. Those skilled in the art will appreciate that other computer terminals can be used in conjunction with the present invention to achieve the same purpose.

Many different computer interfaces may be used to input data into the wireless computer terminal, including a keyboard, a keypad, a scanner, a serial mouse, or any other similar type of input device. A suitable keyboard for use with the wireless computer terminal is a thin Cherry keyboard with a PS/2 interface. An optional plastic keyboard cover protects the keyboard from spills during usage. Other computer interfaces for the wireless computer terminal include a PSC Q6000 scanner with a PS/2 interface, a serial mouse, and a Y-cable to merge the keyboard and the scanner inputs.

Typically, a conventional electrical connection (not shown) between the wireless computer terminal 274 and the power converter provides an interface between the computer terminal 274 and the power converter. Conventional electrical connections such an automobile adaptor plug, or a touch-pin battery charging terminal can be used with a wireless computer terminal 274 to provide an interface with the power converter within the back mounting bracket 222. The power converter, in turn, is connected to the power unit 230 by the power cable (shown in FIG. 10A as 254). The power unit 230 can then be plugged into a standard 120 Volt AC outlet with the power cord 232.

The back mounting bracket 222 or wiring tray also mounts to the bottom side 278 of the horizontal tray 212. The back mounting bracket 222 or wiring tray supports the power converter substantially parallel to and adjacent to the bottom side 278 of the horizontal tray 212. The power converter is supported within the sidewalls of the back mounting bracket 222, which can further support cables (not shown) for other devices connected to the computer terminal 274, such as a mouse, keypad, or other similar devices, or support other power converters for other electrical devices associated with the mobile workstation 210. A series of ventilation holes 282 machined in the sidewall of the back mounting bracket 222 assist in venting heat away from the power converter mounted within the back bracket 222.

The tray housing 218 is also attached the bottom side 278 of the horizontal tray 212. The tray housing 218 is sized to fit over the front mounting bracket 220 and the back mounting bracket 222 leaving sufficient clearance between the topside of the tray housing 218 and both the front bracket 220 and the back bracket 222. Sufficient clearance between the tray housing 218 and the front mounting bracket 220 permits the installation of a keyboard 272 or keypad within the pull-out keyboard tray 250 in the tray housing 218, so that the keyboard 272 does not interfere with the bottom of the front mounting bracket 220 when the pull-out keyboard tray 250 is fully retracted within the tray housing 218 as shown.

The access opening 246 in the side wall of the tray housing 218 permits operator access to various ports or interfaces on the side of the wireless computer terminal 274 through the access window 280 of the front mounting bracket 220. The size of the access opening 246 also permits operator access to actuate the release lever 228 of the gas spring height adjustment mechanism (shown in FIG. 10A as 256) to raise or lower the height of the mobile workstation 210 as shown in FIGS. 9A–9B and FIGS. 11A–11B.

FIG. 12B shows the pull-out keyboard tray 250 in a retracted position within the tray housing 218. The display screen 224 of the mobile workstation 210 is shown in a substantially vertical orientation to the horizontal tray 212. In this configuration, an operator can transport the mobile workstation 210 from one area to another area, or use the top surface 266 of the horizontal tray 212 as a work surface. The length 284 of the horizontal runner beams 260a–b is approximately 21.3 inches.

FIG. 12C shows a front view of the mobile workstation 210 in FIG. 12A. The computer terminal 274 is shown mounted within the front mounting bracket 220 and above the keyboard 272 mounted within the pull-out keyboard tray 250. The height 286 from the top surface 266 of the horizontal tray 212 to the floor is approximately 38.6 inches when the tray 212 is in the lowermost position. The height 288 from the top edge of the display screen 224 in a fully vertical orientation to the floor is approximately 54.5 inches when the tray 212 is in the lowermost position. The width 290 between the outboard ends of the horizontal runner beams 260a–b is approximately 21.4 inches. Other heights 286, 288 for the horizontal tray 212 and the display screen 224 can be attained when the mobile workstation is adjusted for ease of accessibility and visibility.

Figure 13A:
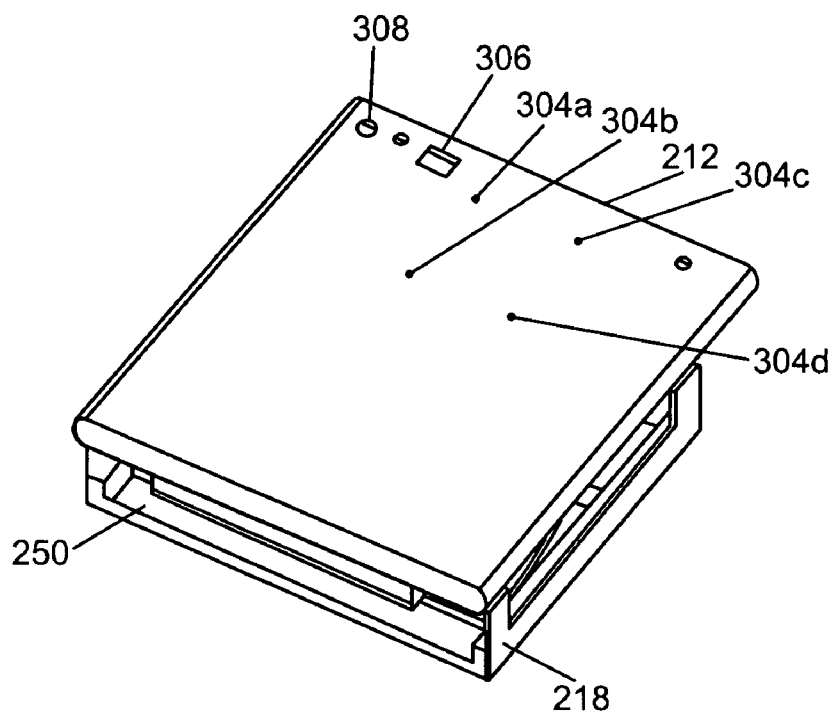
FIG. 13A is a perspective view of the horizontal tray and tray housing of the mobile workstation of FIG. 8.

FIGS. 13A–13D illustrate a series of views of the horizontal tray 212 of the mobile workstation 210 of FIG. 8 with an attached tray housing 218, front mounting bracket 220, back mounting bracket 222, and pull-out keyboard tray 250. FIG. 13A shows a perspective view of the horizontal tray 212 shown in FIG. 8, with an attached tray housing 218 extending from the bottom side of the horizontal tray 212.

Figure 13B:
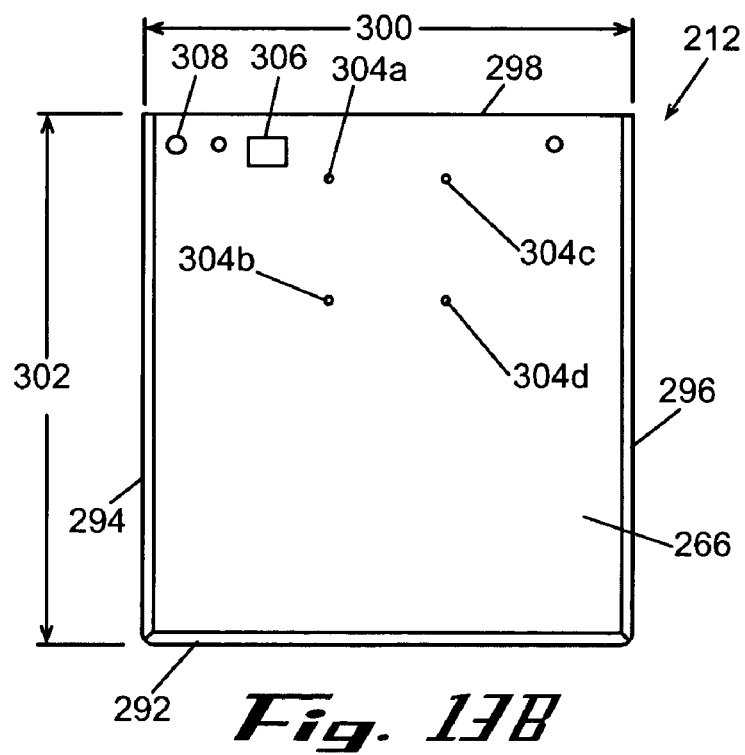
FIG. 13B is a top view of the horizontal tray and mounting bracket of FIG. 13A.

FIG. 13B shows the top view of the horizontal tray 212. The top surface of the horizontal tray 212 is rectangular in shape with rounded edges at the front side 292, the left side 294, and right side 296. The rear side 298 of the horizontal tray 212 has a square edge. The width 300 of the horizontal tray 212 from the left side 294 to the right side 296 is approximately 18.0 inches. The depth 302 of the horizontal tray 212 from the front edge 292 to the rear edge 298 is approximately 19.4 inches. A series of four mounting holes 304a–d is machined into the rear portion of the top surface 266 of the horizontal tray 212 to correspond with a set of mounting bolts (not shown) used to secure the base of the tiltable bracket (shown in FIGS. 12A–12C as 248) to the top surface 266 of the horizontal tray 212. A first hole 306 in the left rear portion of the top surface 266 of the horizontal tray 212 provides access for the display screen cables (not shown) to extend from the display screen 224 to the computer terminal 274 underneath the horizontal tray 212. A second hole 308 machined in the left rear portion of the horizontal tray 212 provides a mount for the terminal antenna 234 permitting the wireless computer terminal 274 to communicate with a computer network (shown in FIG. 8 as 238) via radio frequency communication channel (shown in FIG. 8 as 236).

Figure 13C:
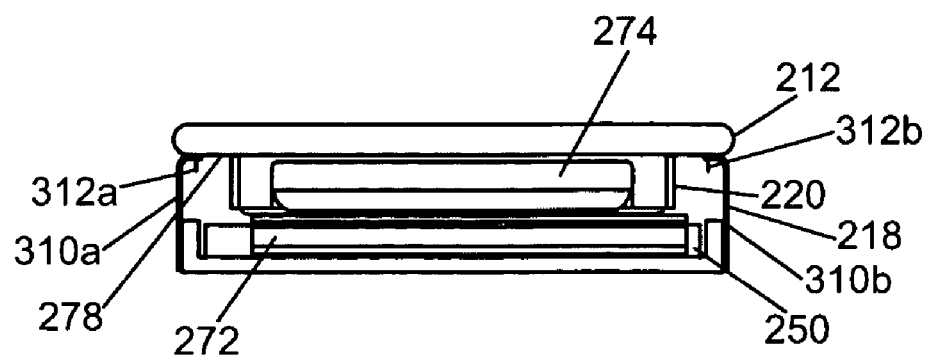
FIG. 13C is a front view of the horizontal tray and mounting bracket of FIG. 13A with an installed wireless computer terminal and keyboard.

FIG. 13C shows the front view of the horizontal tray 212 shown in FIG. 13A, with a wireless computer terminal 274 within the front mounting bracket 220, and a keyboard 272 within the pull-out keyboard tray 250 mounted to the tray housing 218. Each side wall 310a–b of the tray housing 218 curves inward at the top portion of the side wall providing a mounting lip 312a–b to attach the tray housing 218 to the bottom side 278 of the horizontal tray 212. Holes (not shown) are machined in the mounting lip 312a–b to correspond with bolts (not shown) to attach the tray housing 218 securely to the bottom side 278 of the horizontal tray 212.

A pull-out keyboard tray 250 is supported between the side walls 310a–b of the tray housing 218 and substantially parallel to the top side of the tray housing 218. The pull-out tray 250 can be extended or retracted from the front of the tray housing 218. As described previously, conventional rollers (not shown) mounted on the bottom of the pull-out tray 250 correspond with guide slots (not shown) mounted or machined into the top side of the tray housing 218. The keyboard 272 fits within the pull-out keyboard tray 250 so that the keyboard 272 does not interfere with the front mounting bracket 220 when the pull-out keyboard tray 250 is retracted within the tray housing 218.

Figure 13D:
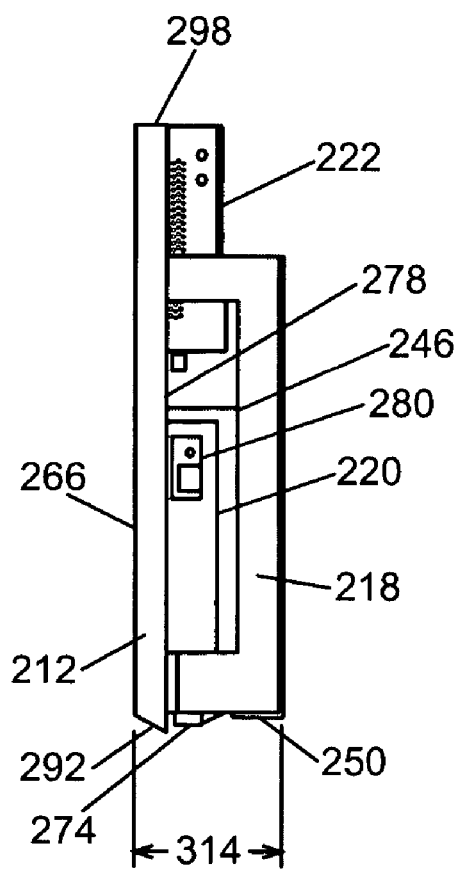
FIG. 13D is a side view of the horizontal tray and mounting bracket of FIG. 13A with an installed wireless computer terminal and keyboard.

FIG. 13D shows a side view of the horizontal tray 212 shown in FIG. 13A, with an attached tray housing 218, front mounting bracket 220, back mounting bracket 222 or wiring tray, and pull-out keyboard tray 250. The front mounting bracket 220 mounts towards the front portion of the horizontal tray 212, providing operator access to the computer terminal 274 from the front edge 292 of the horizontal tray 212. The back mounting bracket 222 or wiring tray mounts towards the rear portion of the horizontal tray 212, flush with the rear edge 298 of the bottom side 278 of the horizontal tray 212. The tray housing 218 mounts near the front edge of the bottom side 278 of the horizontal tray 212, substantially overlapping the front mounting bracket 220 and partially overlapping the back mounting bracket 222. The access opening 246 in the side wall of the tray housing 218 permits operator access to the various ports or interfaces in the side of the wireless computer terminal 274 through the access window 280 of the front mounting bracket 220. The height 314 of the horizontal tray 212 with the attached tray housing 218 measured from the top surface 266 of the horizontal tray 212 to the bottom side of the tray housing 218 is approximately 4.7 inches.

Figure 14A:
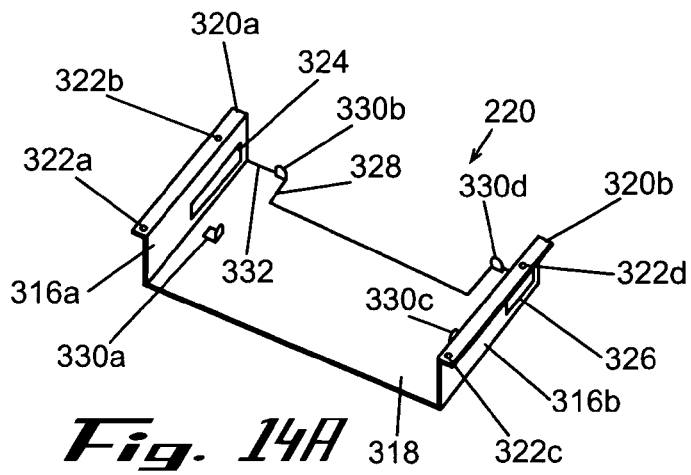
FIG. 14A is a perspective view of the front mounting bracket of the mobile workstation of FIG. 8.

FIGS. 14A–14D illustrate the details of the front mounting bracket 220 shown in FIG. 8. FIG. 14A shows a perspective view of a front mounting bracket 220. The front mounting bracket 220 is sized to receive a wireless computer terminal 274 between two side walls 316a–b and on the top surface 318 of the front bracket 220. Each side wall 316a–b of the front bracket 220 is shaped with a mounting lip 320a–b extending along the top of each side wall 316a–b for mounting the front bracket 220 to the bottom surface 278 of the horizontal tray 212. Two bolt holes 322a–d are machined through each mounting lip 320a–b to receive bolts (not shown) attaching the front bracket 220 to the bottom surface 278 of the horizontal tray 212. Access windows 324, 326 are cut into each side wall 316a–b of the front bracket 220 to permit user access to the ports or interfaces on each side of the wireless computer terminal 274. An elongated access opening 328 along the rear portion of the front bracket 220 permits user access to the ports or interfaces on the bottom of the wireless computer terminal 274. Four tongue protrusions 330a–d from the top surface 318 of the front bracket 220 position the wireless computer terminal 274 within the front bracket, between the side walls 316a–b and flush against the rear edge 132 of the front bracket 220. Two of the tongue protrusions 330b, 330d extend from and are parallel to the rear edge 332 of the front bracket 220 to prevent the wireless computer terminal 274 from extending past the rear edge 332 of the front bracket 220. The other two tongue protrusions 330a, 330d extend upward from the top surface 318 of the front bracket 220 and run parallel with the side walls 316a–b of the front bracket 220 to position the wireless computer terminal 274 between the side walls 316a–b of the front bracket 220 and towards the center portion of the front bracket 220. The tongue protrusions 330a–d are used to position the wireless computer terminal 274 within the front bracket 220. Other types of positioning structures or methods may be used in accordance with the present invention.

Figure 14B:
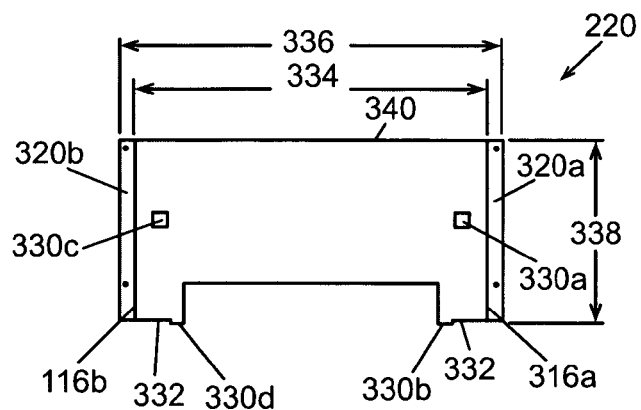
FIG. 14B is a top view of the front mounting bracket of FIG. 14A.

FIG. 14B shows a top view of the front mounting bracket 220 in FIG. 14A. The front mounting bracket 220 can be manufactured from 1/16 inch thickness sheet steel, or any other suitable material. The width 334 of the front bracket 220 measured from the interior of the left sidewall 316a to the interior of the right sidewall 316b is approximately 14.3 inches. The width 336 of the front bracket 220 measured from the outboard end of the left sidewall mounting lip 320a to the right sidewall mounting lip 320b is approximately 15.5 inches. The depth 338 of the front bracket 220 measured from the front edge 340 to the rear edge 332 is approximately 7.4 inches.

Figure 14C:
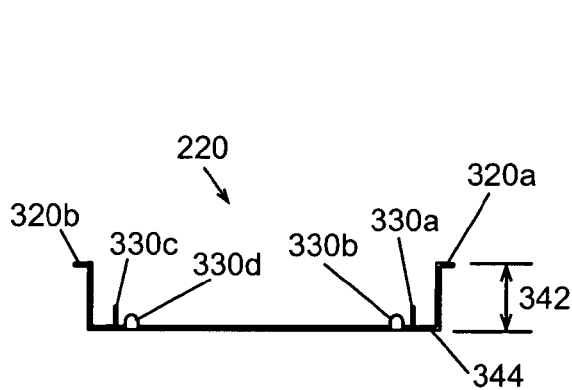
FIG. 14C is a front view of the front mounting bracket of FIG. 14A.

FIG. 14C shows a front view of the front mounting bracket 220 shown in FIG. 14A. The height 342 of the front mounting bracket 220 measured from the top of either mounting lip 320a–b to the bottom side 344 of the front bracket 220 is approximately 2.522 inches.

Figure 14D:
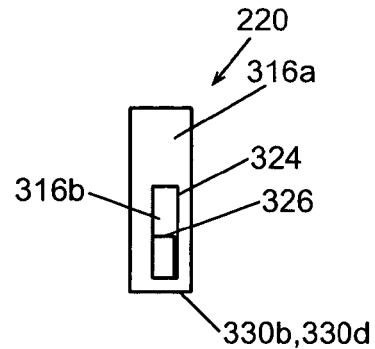
FIG. 14D is a side view of the front mounting bracket of FIG. 14A.

FIG. 14D shows a side view of the front mounting bracket 220 shown in FIG. 14A. The access windows 324, 326 cut into the side walls 316a–b of the front bracket 220 are sized to permit access to ports or interfaces on the sides of the wireless computer terminal (shown in FIG. 13D as 274).

Figure 15A:
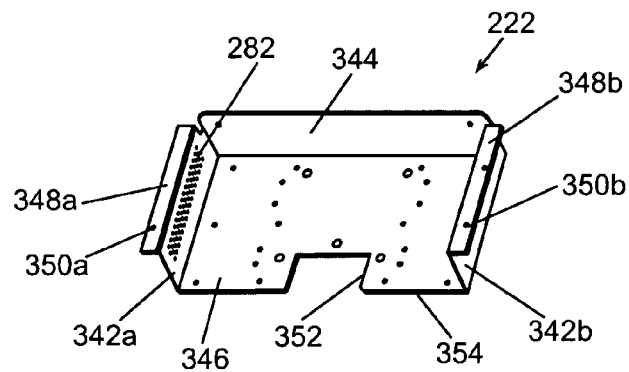
FIG. 15A is a perspective view of the back mounting bracket of the mobile workstation of FIG. 8.

FIGS. 15A–15D illustrate the details of the back mounting bracket 222 or wiring tray shown in FIG. 8. FIG. 15A shows a perspective view of a back mounting bracket 222 or wiring tray. The back mounting bracket 222 or wiring tray is sized to receive a power converter (shown within the back mounting bracket 222 in FIG. 12B as 276) between two side walls 342a–b, a rear wall 344, and the top surface 346 of the back mounting bracket 222. The back mounting bracket 222 or wiring tray can also support associated cables or other power converters associated with the mobile workstation 210. The side walls 342a–b of the back bracket 222 are shaped with a mounting lip 348a–b extending along the top of each side wall 142a–b for mounting the back bracket 222 to the bottom surface (shown in FIG. 13D as 278) of the horizontal tray (shown in FIG. 13D as 212). A single bolt hole 350a–b is machined through each curved mounting lip 348a–b to receive bolts (not shown) attaching the back mounting bracket 222 to the bottom surface 278 of the horizontal tray 212. The series of ventilation holes 282 machined into the side walls 342a–b of the back bracket 222 permit the ventilation of heat from the power converter 276 within the back bracket, allowing subsequent cooling of the power converter 276.

An access window 352 cut into the middle portion of the front edge 354 of the top surface 346 of the back bracket 222 accommodates the vertical beam (shown in FIG. 10A–10B as 226). The vertical beam 226 extends upward from the chassis 216 and fits into the access window 352.

Figure 15B:
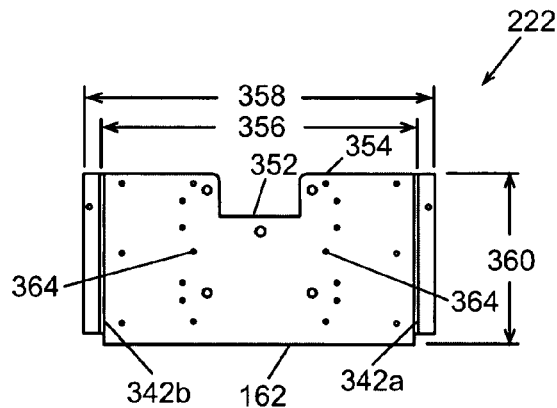
FIG. 15B is a top view of the back mounting bracket of FIG. 15A.

FIG. 15B shows a top view of the back mounting bracket 222 or wiring tray shown in FIG. 15A. The back mounting bracket 222 or wiring tray can be manufactured from 1/16 inch thickness sheet steel, or any other suitable material. The interior width 356 of the back bracket 222 measured from the interior of the left sidewall 342a to the interior of the right sidewall 342b is approximately 0.13.8 inches. The exterior width 358 of the back bracket 222 measured from the outboard end of the left sidewall 342a mounting lip 348a to the outboard end of the right sidewall 342b mounting lip 348b is approximately 15.5 inches. The depth 360 of the back bracket 222 measured from the front edge 354 of the back bracket 222 to the rear edge 362 of the back bracket 222 is approximately 7.5 inches. A series of bolt holes 364 are drilled in the top surface 346 of the back bracket 222 to mount the battery pack 276 to the back mounting bracket 222. A corresponding series of bolts (not shown) pass through the bolt holes 364 attaching the battery pack 276 to the top surface 346 of the back bracket 222. Other holes 365 shown in the top surface 346 of the back bracket 222 are used for tie-wraps to secure loose cables in the back mounting bracket 222 or wiring tray.

Figure 15C:
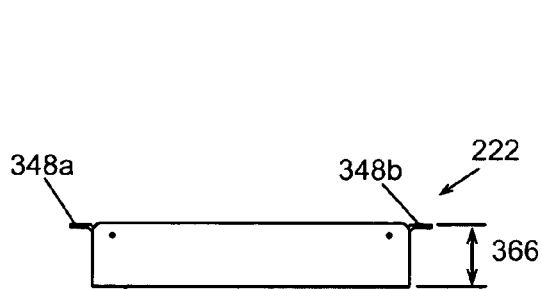
FIG. 15C is a front view of the back mounting bracket of FIG. 15A.

FIG. 15C shows a front view of the back mounting bracket 222 or wiring tray shown in FIG. 15A. The height 366 of the back mounting bracket 222 measured from the top of either mounting lip 348a–b to the bottom side 368 of the back bracket 222 is approximately 2.8 inches.

Figure 15D:
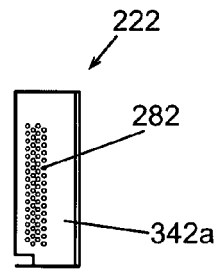
FIG. 15D is a side view of the back mounting bracket of FIG. 15A.

FIG. 15D shows a side view of the back mounting bracket 22 in FIG. 15A. The ventilation holes 282 in the center portion of the left sidewall 342a are selectively sized and shaped to permit sufficient ventilation of heat from the power converter 276, resulting in the subsequent cooling of the power converter 276.

Figure 16:
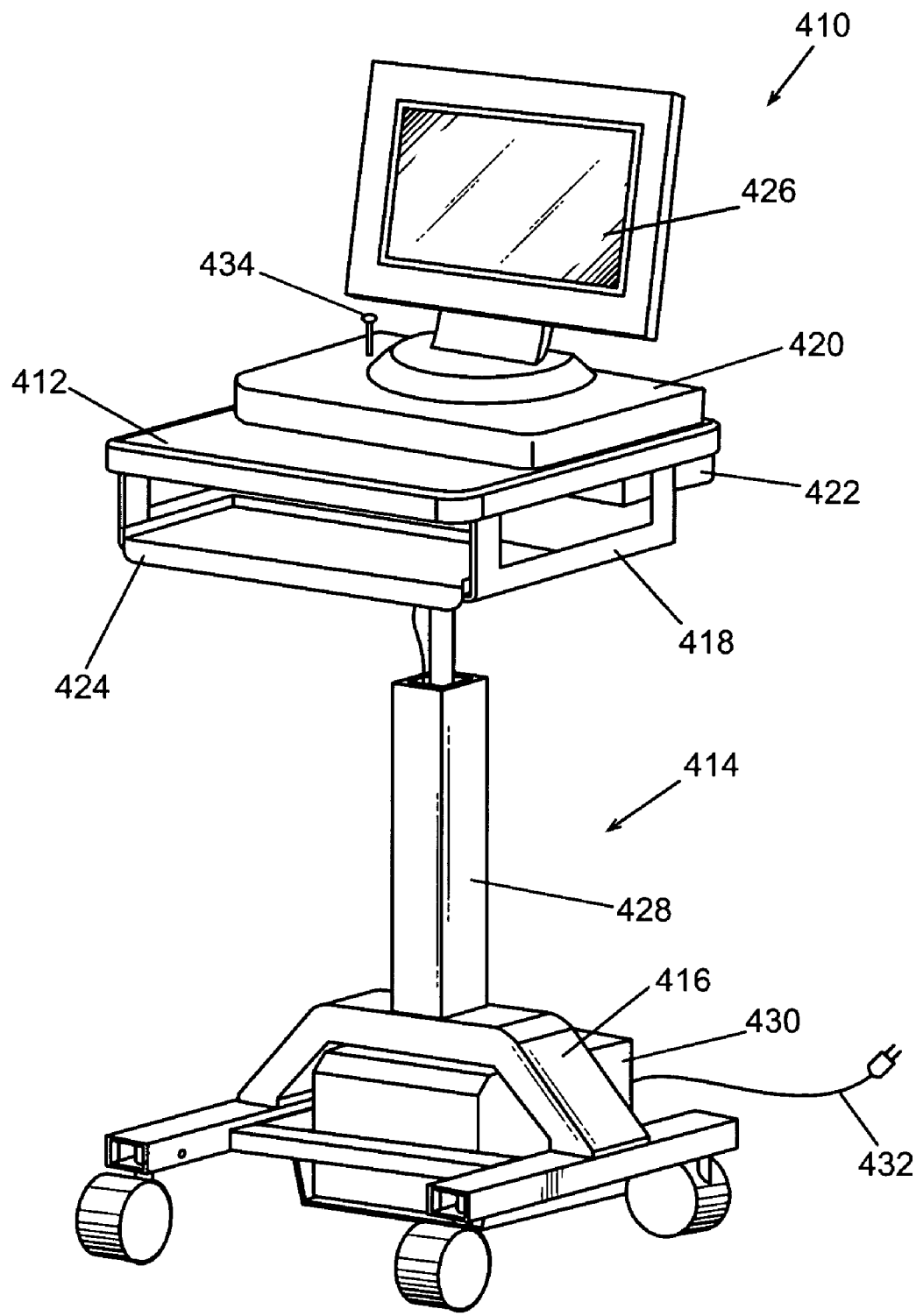
FIG. 16 is a front perspective view of yet another embodiment of a mobile workstation.
Figure 11:
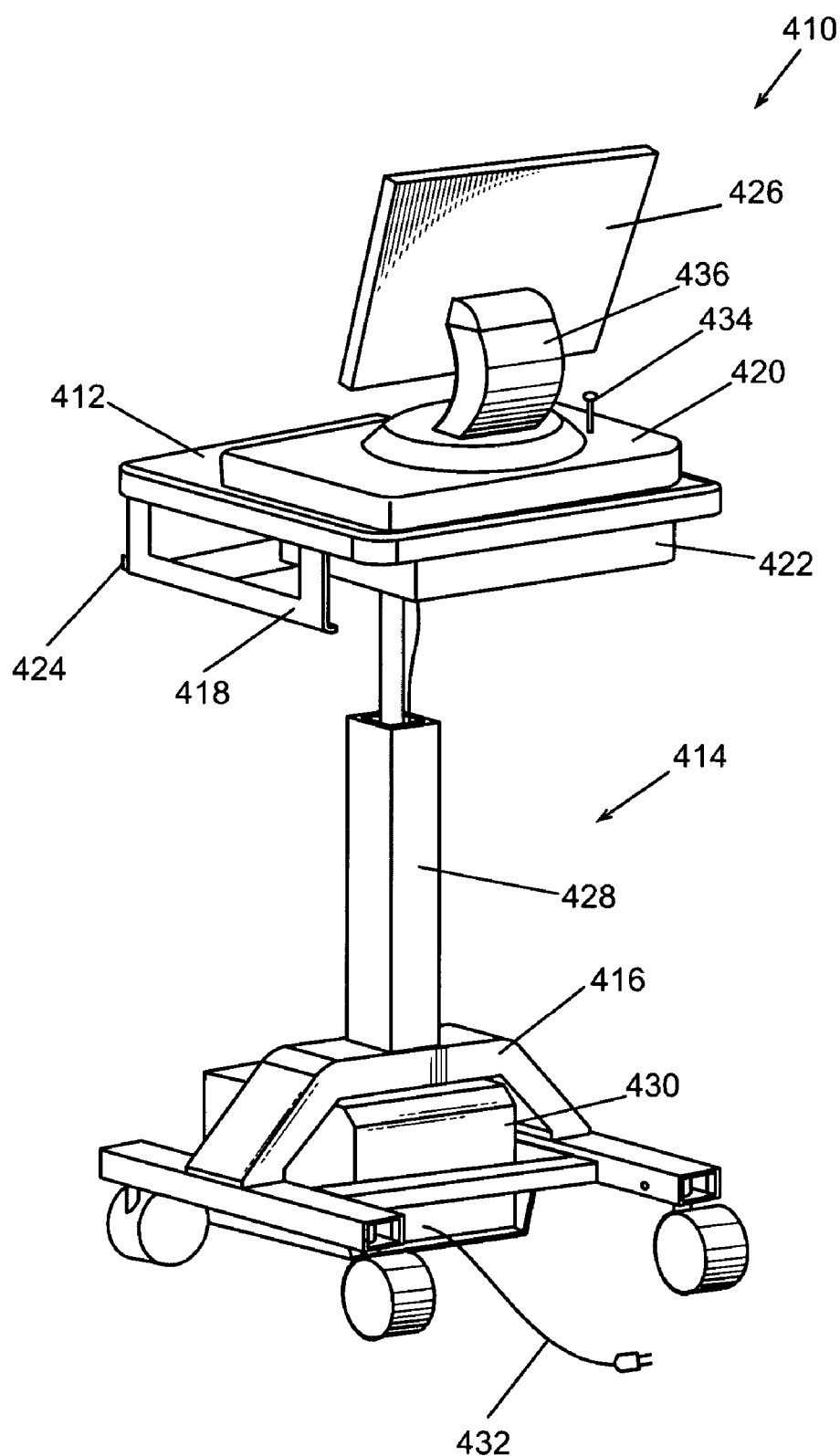

FIG. 16 is a front perspective view of another embodiment of a mobile workstation 410. The mobile workstation 410 includes an adjustable-height horizontal tray 412 supported by a chassis 414. The chassis 414 includes a dolly assembly 416 that allows an operator, such as a medical practitioner, to easily push the mobile workstation 410 from place to place. The horizontal tray 412 includes an underside tray housing 418, a mounting bracket 420, and an underside back mounting bracket 422.

The tray housing 418 supports a keyboard (not shown) or keypad for a wireless computer terminal (not shown) in a pull-out keyboard tray 424. The wireless computer terminal mounts within the mounting bracket 420. The back mounting bracket 422 supports a power converter (not shown) that converts conventional AC or battery power to suitable electrical power for the wireless computer terminal and a display screen 426. The tiltable display screen 426 attaches to the top of the horizontal tray 412 while connecting to the wireless computer terminal. The back mounting bracket 222 can also support associated cables or other power converters associated with the mobile workstation 210.

The chassis 414 includes a vertical beam 428 connecting the horizontal tray 412 to the dolly assembly 416. The vertical beam 428 includes a gas-spring height adjustment mechanism (not shown) and a release lever (not shown) for adjusting the length of the beam 428 and, thus, the height of the horizontal tray 412 above the dolly assembly 416. For example, the chassis 414 may be a chassis model previously described and shown in FIG. 8.

The mobile workstation 410 also carries a power unit 430 including a battery charger, an extended-life battery, a power cord 432, and a recoil mechanism that can retract the power cord when the cord is not plugged into an AC outlet. The power unit 430 is located on the lower end of the chassis 414. For example, the power unit 430 may reside between two metal beams in the dolly assembly 416 at the lower end of the chassis 414. A suitable power unit 430 is a 26 Amp-Hour battery providing a regulated 10–16 Volt output at 40 watts with an automatic low power cut-off. The extended-life battery may be a 12-Volt sealed lead acid battery, and the battery charger may be a 120-Volt AC to 16-Volt DC converter.

The power unit 430 typically includes a first status-indicator light to inform the user when the AC power is being supplied, a second status-indicator light to inform the user when the battery needs recharging, and a seven-level battery status-indicator light. The power unit 430 may also include a sound indicator that beeps to inform the user when the battery needs recharging. When plugged into an AC outlet, the battery charger will charge both the extended-life battery and operate the wireless computer terminal. The extended-life battery can be recharged by plugging the power cord 432 into a standard 120-volt AC outlet. When not in use, the recoil mechanism automatically recoils the power cord 432 into the power unit 430.

The wireless computer terminal inside the mobile workstation 410 communicates through a radio transmitter/receiver terminal antenna 434 attached to the top of the horizontal tray 412. The terminal antenna 434 is operable for communicating over an approved radio frequency. In particular, the wireless computer terminal may establish a radio-frequency communication channel with a distributed patient-care computer network as previously shown and described in FIG. 8.

FIG. 17 is a rear right side perspective view of the mobile workstation 410 in FIG. 16. A tiltable bracket 436 attaches the display screen 426 to the horizontal tray 412. The tiltable bracket 436 maintains the display screen 426 in a number of selectable rotational positions relative to the tray 412. The rotational range of the tiltable bracket 436 is preferably about 30 degrees rearward from vertical. That is, the tiltable bracket 436 preferably allows the display screen 426 to be rotated left to right. The tiltable bracket 436 could also be configured to allow the display screen 426 to rotate forward through a similar rotational range.

It should be understood that the term "substantially vertical" may include a range about a strictly vertical orientation, represented by a 30 degree range. For example, the term "substantially vertical" includes configurations in which the bracket 436 maintains the display screen 426 in a strictly vertical orientation, or at a fixed rotational orientation with a vertical component, or within a range of rotational orientations including orientations that include vertical components. Alternatively, the display screen 426 could be supported in a substantially horizontal position, for example by a drawer or pull-out tray located above or under the horizontal tray 412. Other locations for the display screen 426 may be preferred in certain environments. For example, the display screen 426 could be mounted to the side of the horizontal tray 412, to the underside of the horizontal tray 412, to the dolly assembly 416, to the vertical beam 428, and so forth.

The tiltable bracket 436 imparts sufficient rotational resistance to maintain the display screen 426, with an associated computer terminal (not shown), at any of the rotational aspects within the rotational range defined by the tiltable bracket 436. At the same time, the rotational resistance imparted by the tiltable bracket 436 is pliant enough to allow the operator to change the rotational orientation of the display screen 426 with one hand. For example, the operator may easily adjust the angle of the display screen 426 to avoid glare on the display screen 426.

Figure 18:
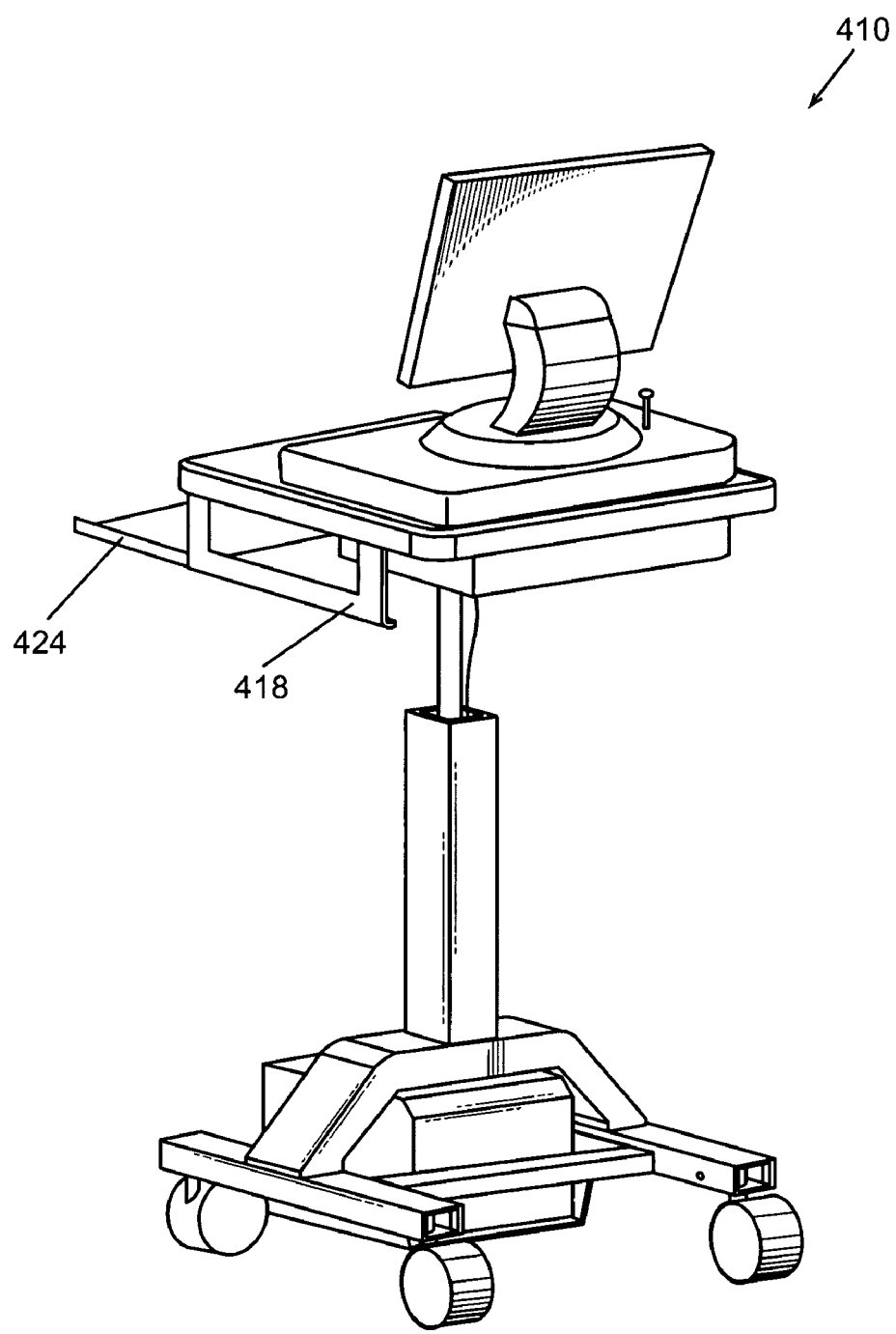
FIG. 18 is a rear right side perspective view of the mobile workstation in FIG. 16 with a pull-out keyboard tray in the extended position.

FIG. 18 is a rear right side perspective view of the mobile workstation 410 in FIG. 16 with the pull-out keyboard tray in the extended position. The pull-out keyboard tray 424 slides from an inner position, shown in FIGS. 16–17, to an outer position, shown in FIG. 18, along conventional rollers (not shown) within a conventional roller guide slots (not shown). Typically, rollers mounted to the bottom side of the keyboard tray 424 fit within roller guide slots attached to the top side of the tray housing 418. A keyboard (not shown) fits within the pull-out keyboard tray 424. The pull-out keyboard tray 424 is to detent when fully extended away from the front edge of the tray housing 418, permitting the operator to type on the keyboard without the keyboard tray 424 sliding back into the tray housing 418. When the pull-out keyboard tray 424 is in the retracted position, the keyboard tray 424 will not slide out during movement or transport of the mobile workstation 410.

As shown in FIG. 18, the pull-out keyboard tray 424 can be extended outward from the front end of the tray housing 418. The rollers on the bottom of the pull-out keyboard tray 424 permit the pull-out tray 424 to roll forward within the roller guide slots along the length of the top side of the tray housing 418. The roller guide slots have a physical stop at the front end of the tray housing 418. When a roller makes contact with the physical stop at the front end of the tray housing 418, the pull-out keyboard tray 424 cannot be extended any further from the front edge of the tray housing 418.

Figure 19:
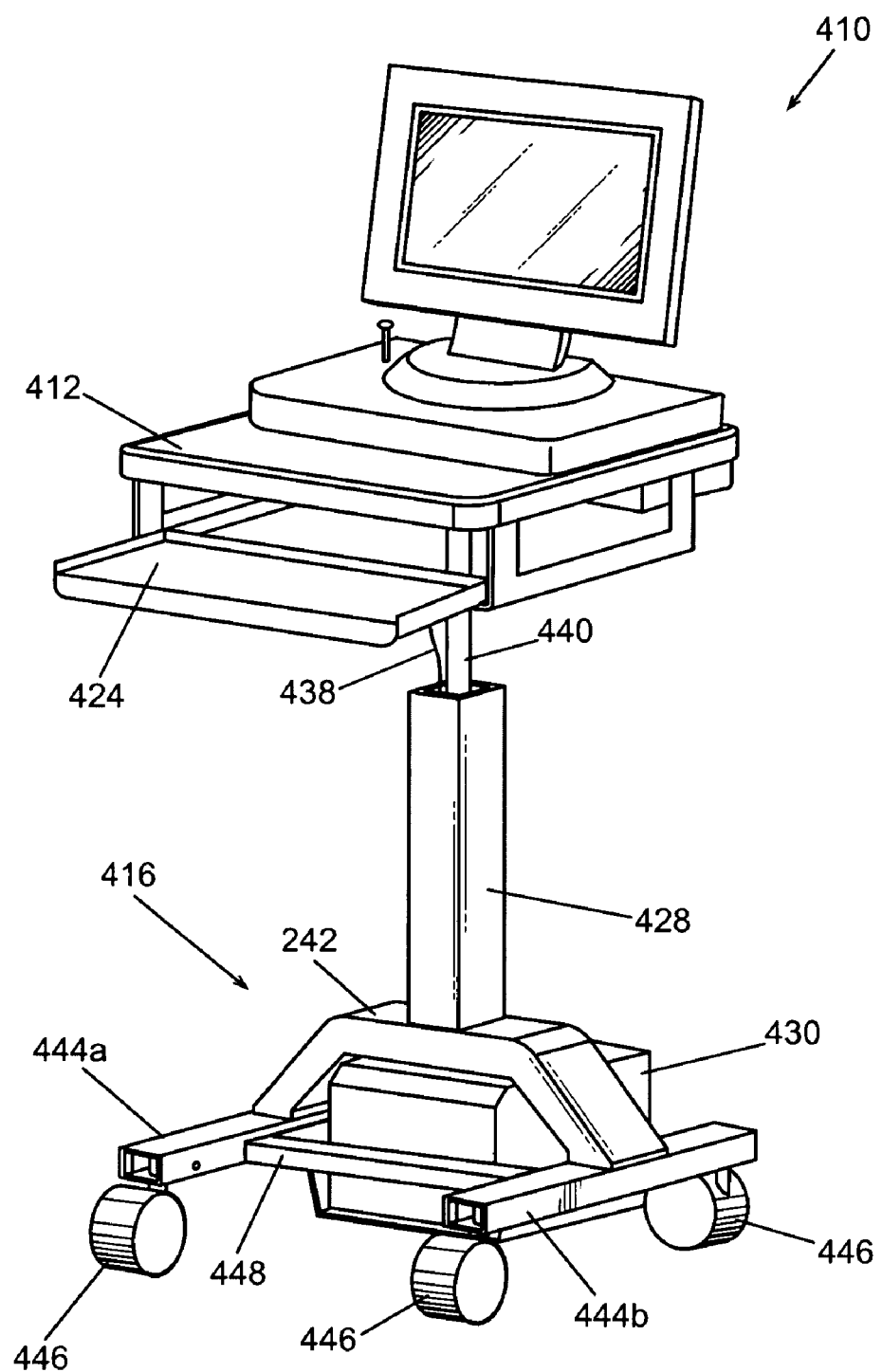
FIG. 19 is a front right side perspective view of the mobile workstation in FIG. 16 with the pull-out keyboard tray in the extended position.

FIG. 19 is a front right side perspective view of the mobile workstation 410 in FIG. 16 with the pull-out keyboard tray 424 in the extended position. The top portion of a rectangular cover for the vertical beam 428 has been removed, showing an underlying shaft 438 and a power cable 440 connecting the power unit 430 to the power converter (not shown). This shaft 438 connects to the gas-spring height adjustment mechanism (not shown) that allows adjustment of the height of the horizontal tray 412. The gas-spring height adjustment mechanism, which is located at the bottom of the vertical beam 428, sits on top of the dolly assembly 416. This dolly assembly 416 includes an arched cross-beam 442 that connects to two horizontal runner beams 444a–b. Two casters, represented by the caster 446, are connected to the bottom sides of each horizontal runner beam 444a–b. For example, a suitable size caster is a conventional 5" caster. The power unit 430 is mounted below the arched cross beam 442 with a support bracket 448, which connects between the horizontal runner beams 444a–b.

Figure 20:
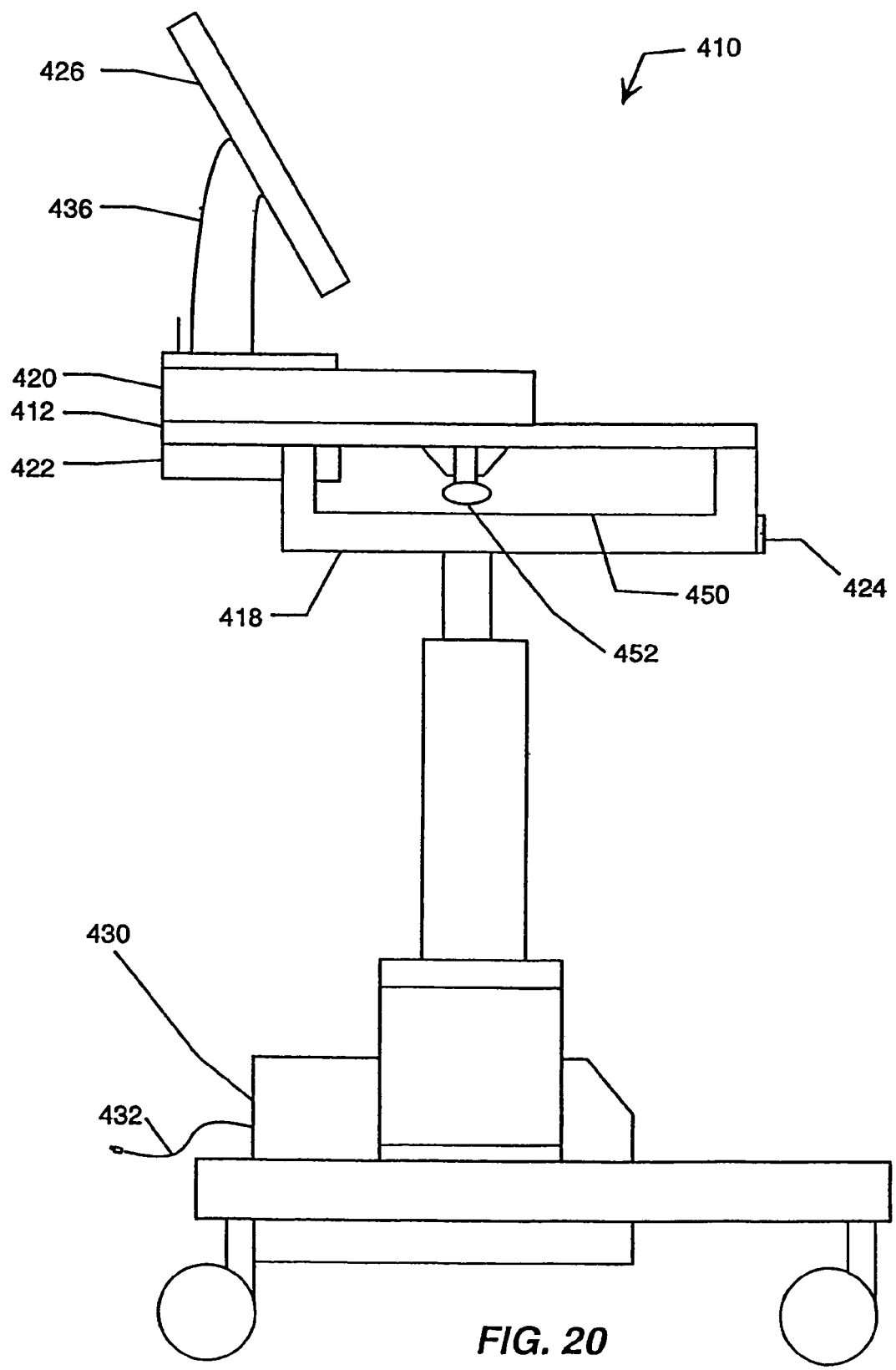
FIG. 20 is a side view of the mobile workstation shown in FIG. 16.

FIG. 20 is a side view of the mobile workstation 410 shown in FIG. 16. The mounting bracket 420 attaches to the top surface of the horizontal tray 412 permitting a wireless computer terminal (not shown) to be stored on the top of the horizontal tray 412. The tiltable bracket 436, supporting the display screen 426, mounts to the top surface of the mounting bracket 420. A touch-pin display interface (not shown) located on the back of the wireless computer terminal provides an interface between the computer terminal and the display screen 426.

The tray housing 418 mounts to the underside of the horizontal tray 412. The pull-out keyboard tray 424 supporting a keyboard (not shown), mounts to the front portion of the top surface of the tray housing 418. The wireless computer terminal may include a communication interface, such as an optical interface, for communicating data between the computer terminal and the keyboard. A conventional electrical connection allows the keyboard to communicate keystrokes to the computer terminal. This type of operation permits an operator to easily remove the computer terminal from the mounting bracket 420, or to remove the keyboard from the pull-out keyboard tray 424.

The back mounting bracket 422 or wiring tray attaches to the rear portion of the underside of the horizontal tray 412. The back mounting bracket 422 or wiring tray supports the power converter (not shown) for supplying power to the wireless computer terminal. A touch-pin battery charging terminal (not shown) or other conventional electrical connection, such as an automobile adaptor plug, located on the back of the wireless computer terminal provides an interface between the computer terminal and the power converter within the back mounting bracket 422. The power converter, in turn, is connected to the power unit 430 by the power cable (shown in FIG. 19 as 440). The power unit 430 can then be plugged into a standard 120 Volt AC outlet with the power cord 432.

An access opening 450 in the side of the tray housing permits operator access to actuate a release lever 452 for raising and lowering the horizontal tray 412. The release lever 452 operates the gas-spring height adjustment mechanism (not shown). Typically, the release lever 452 has a tee or a paddle on the end, so that an operator can conveniently actuate the release lever 452 thereby raising or lowering the gas-spring height adjustment mechanism.

In view of the foregoing, it will be appreciated that the invention provides a mobile workstation that includes an adjustable-height horizontal tray and a vertically-mounted docking station mounted to the horizontal tray. The mobile workstation also carries a power converter and a power unit including a battery charger and an extended-life battery for a wireless computer terminal stored within the docking station. It will also be appreciated that the invention provides a mobile workstation that includes an adjustable-height horizontal tray mounted on a chassis, a vertically-mounted display screen mounted to the horizontal tray, a wireless computer terminal and battery converter mounted to the horizontal tray, a pull-out keyboard tray mounted beneath the computer terminal, and a power unit mounted to the chassis. The power unit also includes a battery charger and an extended-life battery for the wireless computer terminal. It should be understood that the foregoing relates only to the exemplary embodiments of the present invention, and that numerous changes may be made therein without departing from the spirit and scope of the invention as defined by the following claims.

The invention claimed is:

1. A mobile workstation, comprising:
   a moveable chassis;
   a tray supported by the chassis and having an upper surface defining a substantially horizontal work surface and a lower surface comprising an input device tray proximate to the lower surface; and
   a docking station for a computing device supported by the tray,
   wherein the docking station is tiltable relative to the upper surface of the tray.

2. The mobile workstation of claim 1, wherein the input device tray is a pull-out tray.

3. The mobile workstation of claim 1, wherein the input device tray is an adjustable tray.

4. The mobile workstation of claim 1, wherein the input device tray is a height adjustable tray.

5. The mobile workstation of claim 1, further comprising:
   a power unit supported by the chassis for supplying power to the computing device.

6. The mobile workstation of claim 1, further comprising a monitoring device, the monitoring device supported about the moveable chassis.

7. The mobile workstation of claim 1, further comprising a medical device, the medical device supported about the moveable chassis.

8. The mobile workstation of claim 1, further comprising a tiltable display, wherein the tiltable display is used to view medical images.

* * * * *